(12) United States Patent
Huang et al.

(10) Patent No.: US 9,745,611 B2
(45) Date of Patent: Aug. 29, 2017

(54) METHODS AND KITS FOR IDENTIFYING MICROORGANISMS IN A SAMPLE

(71) Applicant: GENEWIZ INC., South Plainfield, NJ (US)

(72) Inventors: Jun Huang, Somerset, NJ (US); Zhenzhen Zhou, Madison, NJ (US); Hairong Duan, Suzhou (CN); Xin Wu, Suzhou (CN); Shihong Li, Berkeley Heights, NJ (US)

(73) Assignee: GENEWIZ INC., South Plainfield, NJ (US)

( * ) Notice: Subject to any disclaimer, the term of this patent is extended or adjusted under 35 U.S.C. 154(b) by 395 days.

(21) Appl. No.: 14/270,805

(22) Filed: May 6, 2014

(65) Prior Publication Data

US 2015/0322492 A1    Nov. 12, 2015

(51) Int. Cl.
*C12Q 1/04* (2006.01)
*C12Q 1/68* (2006.01)

(52) U.S. Cl.
CPC ............ *C12Q 1/04* (2013.01); *C12Q 1/689* (2013.01); *C12Q 2600/16* (2013.01)

(58) Field of Classification Search
CPC ....... C12Q 1/689; C12Q 2600/16; C12Q 1/04
USPC ............... 435/6.12, 91.1, 91.2; 536/24.33
See application file for complete search history.

(56) References Cited

U.S. PATENT DOCUMENTS

| 2009/0263809 | A1* | 10/2009 | Roberton | ............. | B01D 57/02 435/6.18 |
| 2011/0129830 | A1* | 6/2011 | Ladner | ................. | C12Q 1/6881 435/6.11 |
| 2014/0357499 | A1* | 12/2014 | Gordon | ................ | C12Q 1/6869 506/2 |

OTHER PUBLICATIONS

Lowe et al. (Nucleic Acid Research, 1990, vol. 18(7), p. 1757-1761.*
Nucleic acid sequence search reports (AC: FX841512,FX823815, FX837073, BBQ98675, BBQ98686, BBQ98668).*
Pinto et al., PLOS ONE, vol. 7, iss. 8, pp. e43093; 1-16, Aug. 2012.*
"16S MetaVx Sequencing", Genewiz 2014, downloaded on Mar. 21, 2014 from http://web.genewiz.com/16s-metagenomics-comparison, available online Oct. 18, 2013.
Baker, G.C., et al., "Review and re-analysis of domain-specific 16S primers", Journal of Microbiological Methods 55, 2003, pp. 541-555.
Caporaso, J. G., et al., "Global patterns of 16S rRNA diversity at a depth of millions of sequences per sample", PNAS, Mar. 15, 2011, vol. 108, supp. 1, pp. 4516-4522.
Claesson, M.J., et al., "Comparison of two next-generation sequencing technologies for resolving highly complex microbiota composition using tandem variable 16S rRNA gene regions", Nucleic Acids Research, 2010, vol. 38, No. 22, e200, pp. 1-13.
Klindworth, A., et al., "Evaluation of general 16S ribosomal RNA gene PCR primers for classical and next-generation sequencing-based diversity studies", Nucleic Acids Research, 2012, pp. 1-11, downloaded from http://nar.oxfordjournals.org/ by guest on Oct. 28, 2013.
Lorenz, P. and Eck, J., "Metagenomics and industrial applications", Nature, Jun. 2005, vol. 3, pp. 510-516.
Nossa, C.W., et al., "Design of 16S rRNA gene primers for 454 pyrosequencing of the human foregut microbiome", World J. Gastroenterol, Sep. 7, 2010, 16(33); 4135-4144.
Ronaghi, M., "Pyrosequencing Sheds Light on DNA Sequencing", Genome Res., 2001, vol. 11, pp. 3-11.
Ronaghi, M., et al., "A Sequencing Method Based on Real-Time Pyrophosphate", Science, Jul. 17, 1998, vol. 281, No. 5375, pp. 363-365.
Sim, K., et al., "Improved Detection of Bifidobacteria with Optimised 16S rRNA-Gene Based Pyrosequencing", PLoS One, Mar. 2012, vol. 7, issue 3, e32543, pp. 1-7.
Soergel, D. AW., et al., "Short Communication—Selection of primers for optimal taxonomic classification of enviromental 16S rRNA gene sequences", The ISME Journal, 2012, vol. 6. pp. 1440-1444.
Voelkerding, K. V., et al., "Next-Generation From Basic Research to Diagnostics", Clinical Chemistry, 2009, vol. 55, No. 4, pp. 641-658.
Wang, Y., et al., "Conservative Fragments in Bacterial 16S rRNA Genes and Primer Design for 16S Ribosomal DNA Amplicons in Metagenomic Studies", PLoS ONE, Oct. 2009, vol. 4, issue 10, e7401, pp. 1-9.
Wuyts, J., "The European database on small subunit ribosomal RNA", Nucleic Acids Research, 2002, vol. 30, No. 1, pp. 183-185.

* cited by examiner

*Primary Examiner* — Cynthia B Wilder
(74) *Attorney, Agent, or Firm* — Scully Scott Murphy & Presser

(57) ABSTRACT

Disclosed herein are compositions with uniquely designed oligonucleotide primers for identifying a plurality of microorganisms in a sample, and improved methods for detection of microbial populations from diverse biological and environmental samples.

23 Claims, 8 Drawing Sheets

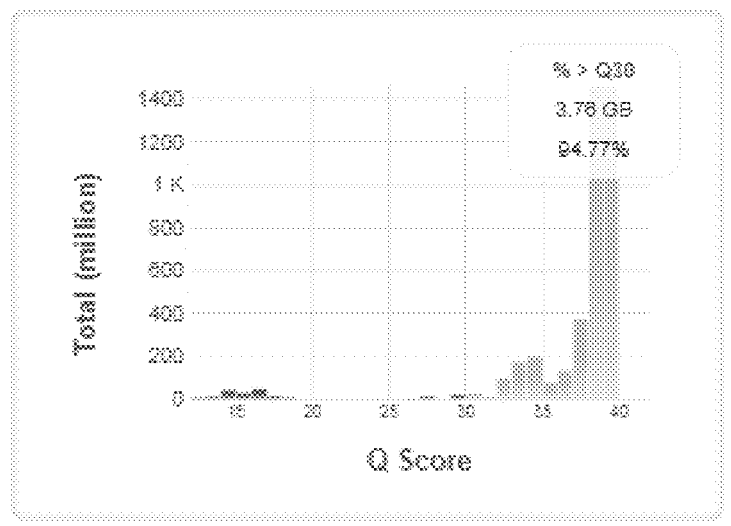
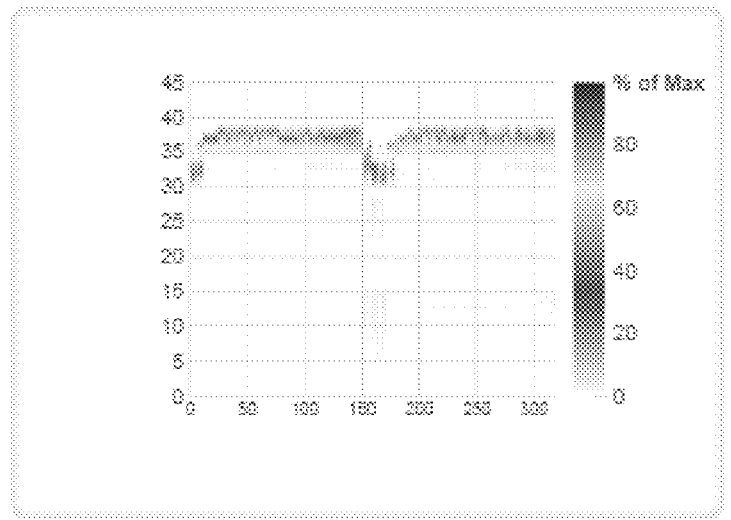
Fig. 4 (con't)

| A | READS (M) | VX1344-OLD | VX1344-V4 | detection | VX1344-V3 | detection | VX1344-V3-V4 | detection | VX1344-V4-V5 | detection |
|---|---|---|---|---|---|---|---|---|---|---|
| | Kingdom | 0.2 | 0.2 | | 0.2 | | 0.2 | | 0.2 | |
| | Kingdom | 1 | 1 | 100% | 2 | 200% | 2 | 200% | 2 | 200% |
| | Phylum | 6 | 11 | 183% | 8 | 133% | 7 | 117% | 12 | 200% |
| | Class | 8 | 23 | 288% | 18 | 225% | 17 | 213% | 24 | 300% |
| | Order | 11 | 38 | 345% | 29 | 264% | 29 | 264% | 38 | 345% |
| | Family | 13 | 61 | 469% | 50 | 385% | 49 | 377% | 62 | 477% |
| | Genus | 15 | 70 | 467% | 56 | 373% | 55 | 367% | 68 | 453% |

| B | READS (M) | VX1345-OLD | VX1345-V4 | detection | VX1345-V3 | detection | VX1345-V3-V4 | detection | VX1345-V4-V5 | detection |
|---|---|---|---|---|---|---|---|---|---|---|
| | Kingdom | 0.2 | 0.2 | | 0.2 | | 0.2 | | 0.2 | |
| | Kingdom | 1 | 2 | 200% | 2 | 200% | 2 | 200% | 2 | 200% |
| | Phylum | 6 | 7 | 117% | 7 | 117% | 7 | 117% | 7 | 117% |
| | Class | 7 | 11 | 157% | 11 | 157% | 11 | 157% | 11 | 157% |
| | Order | 8 | 18 | 225% | 19 | 238% | 19 | 238% | 18 | 225% |
| | Family | 9 | 26 | 289% | 27 | 300% | 27 | 300% | 26 | 289% |
| | Genus | 10 | 29 | 290% | 32 | 320% | 32 | 320% | 29 | 290% |

| | VX1348-OLD | VX1348-V4 | detection | VX1348-V3 | detection | VX1348-V3-V4 | detection | VX1348-V4-V5 | detection |
|---|---|---|---|---|---|---|---|---|---|
| READS (M) | 0.2 | 0.2 | | 0.2 | | 0.2 | | 0.2 | |
| Kingdom | 2 | 2 | 100% | 2 | 100% | 2 | 100% | 2 | 100% |
| Phylum | 22 | 22 | 100% | 18 | 82% | 18 | 82% | 23 | 105% |
| Class | 50 | 50 | 100% | 45 | 90% | 47 | 94% | 51 | 102% |
| Order | 90 | 87 | 97% | 81 | 90% | 83 | 92% | 87 | 97% |
| Family | 152 | 151 | 99% | 146 | 96% | 152 | 100% | 151 | 99% |
| Genus | 240 | 235 | 98% | 238 | 99% | 243 | 101% | 241 | 100% |

B

| | VX1349-OLD | VX1349-V4 | detection | VX1349-V3 | detection | VX1349-V3-V4 | detection | VX1349-V4-V5 | detection |
|---|---|---|---|---|---|---|---|---|---|
| READS (M) | 0.2 | 0.2 | | 0.2 | | 0.2 | | 0.2 | |
| Kingdom | 2 | 2 | 100% | 2 | 100% | 2 | 100% | 2 | 100% |
| Phylum | 28 | 31 | 111% | 26 | 93% | 28 | 100% | 33 | 118% |
| Class | 77 | 81 | 105% | 74 | 96% | 75 | 97% | 84 | 109% |
| Order | 133 | 133 | 100% | 125 | 94% | 128 | 96% | 140 | 105% |
| Family | 212 | 216 | 102% | 209 | 99% | 213 | 100% | 220 | 104% |
| Genus | 301 | 305 | 101% | 306 | 102% | 308 | 102% | 324 | 108% |

| | VX1346-OLD | VX1346-V4 | detection | VX1346-V3 | detection | VX1346-V3-V4 | detection | VX1346-V4-V5 | detection |
|---|---|---|---|---|---|---|---|---|---|
| READS (M) | 0.2 | 0.2 | | 0.2 | | 0.2 | | 0.2 | |
| Kingdom | 2 | 2 | 100% | 2 | 100% | 2 | 100% | 2 | 100% |
| Phylum | 6 | 9 | 150% | 9 | 150% | 10 | 167% | 10 | 167% |
| Class | 10 | 20 | 200% | 20 | 200% | 20 | 200% | 21 | 210% |
| Order | 18 | 32 | 178% | 30 | 167% | 30 | 167% | 31 | 172% |
| Family | 23 | 47 | 204% | 55 | 239% | 54 | 235% | 47 | 204% |
| Genus | 30 | 55 | 183% | 66 | 220% | 62 | 207% | 53 | 177% |

B

| | VX1347-OLD | VX1347-V4 | detection | VX1347-V3 | detection | VX1347-V3-V4 | detection | VX1347-V4-V5 | detection |
|---|---|---|---|---|---|---|---|---|---|
| READS (M) | 0.2 | 0.2 | | 0.2 | | 0.2 | | 0.2 | |
| Kingdom | 1 | 2 | 200% | 1 | 100% | 1 | 100% | 2 | 200% |
| Phylum | 4 | 7 | 175% | 7 | 175% | 7 | 175% | 9 | 225% |
| Class | 6 | 18 | 300% | 17 | 283% | 18 | 300% | 20 | 333% |
| Order | 12 | 31 | 258% | 29 | 242% | 30 | 250% | 30 | 250% |
| Family | 19 | 52 | 274% | 51 | 268% | 54 | 284% | 49 | 258% |
| Genus | 32 | 62 | 194% | 61 | 191% | 64 | 200% | 61 | 191% |

Fig. 7

METHODS AND KITS FOR IDENTIFYING MICROORGANISMS IN A SAMPLE

INCORPORATION BY REFERENCE OF SEQUENCE LISTING

The Sequence Listing in the ASCII text file, named as 30587_ST25.txt of 19 KB, created on Apr. 24, 2014, and submitted to the United States Patent and Trademark Office via EFS-Web, is incorporated herein by reference.

BACKGROUND OF THE DISCLOSURE

With as many as $10^{30}$ microbial genomes globally, across multiple different environmental and host conditions, genetic variety both within and between microbiomes is well recognized (Huse et al., *PLoS Genetics* 4(11): e1000255 (2008)). As a result of this variety, characterizing the contents of a microbiome is a challenge for current approaches. First, standard culturing techniques are successful in maintaining only a small fraction of the microorganisms in nature. Means of more direct profiling, such as sequencing, face additional challenges. Both the sheer number of different genomes in a given sample and the degree of homology between members presents a complex problem for identification of species.

Prokaryotic ribosomes are composed of two subunits: a 30S subunit (small subunit) and a 50S subunit (large subunit), which together make up the complete 70S ribosome, where S stands for Svedberg unit for sedimentation rate. The 30S subunit is composed of 16S ribosomal RNA and 21 proteins, while the 50S subunit is composed of two rRNA species, the 5S and 23S rRNAs. The presence of hyper variable regions in the 16S rRNA gene provides a species specific signature sequence which is useful for bacterial identification process. 16S ribosomal DNA sequencing is widely used in microbiology studies to identify the diversity in prokaryotic organisms as well as other organisms and thereby study the phylogenetic relationships between them.

16S RNA genes from microbiota have been used to characterize microbial communities from diverse environments such as soil and gastrointestinal samples. However, methods to improve detection of microorganisms, including increasing the ability to detect microorganisms present in small numbers, identifying and distinguishing microbiota with both high and low conservation of 16S sequences, and improving accuracy of reads, are desired.

BRIEF SUMMARY OF THE DISCLOSURE

Disclosed herein are forward primer sets and reverse primer sets for identifying a plurality of microorganisms in a sample. Each primer set has one or more oligonucleotide primers, and at least one set has multiple primers. Each primer within each set has a domain-specific sequence that is substantially complementary to a conserved domain of a bacterial or archaeal ribosomal 16S DNA sequence adjacent to the V3, V4, or V5 region of the 16S DNA sequence. For each primer set that includes multiple primers, the primers within the set are overlapping primers which are substantially complementary to the same conserved domain, and each primer within the set differs from at least another primer within the set by a frame shift of one to three nucleotides at the 5' end of the domain-specific sequence, such that a forward primer set in combination with a reverse primer set generate frame-shifted amplicons in a polymerase-chain reaction (PCR).

Each primer in a primer set with multiple primers can have at least one random nucleotide adjacent to the 5' start of the domain-specific sequence. Each primer in a primer set with multiple primers can also, or alternatively, have at least one degenerate nucleotide within the domain-specific sequence. In some embodiments, both the forward primer set and the reverse primer set have multiple overlapping primers.

The frame-shifted amplicons generated according to the invention can include amplicons covering (i) the V3 and V4 regions; (ii) the V4 and V5 regions; (iii) the V4 region, and/or (iv) the V3, V4, and V5 regions.

In one example, the domain-specific sequence of each primer of the forward primer set is substantially complementary to the C2-domain of the 16S DNA sequence, and the domain-specific sequence of each primer of the reverse primer set is substantially complementary to the C4-domain of the 16S DNA sequence. These primers, in combination, would amplify the V3-V4 regions of the 16S DNA sequence. In another example, the domain-specific sequence of each primer of the forward primer set is substantially complementary to the C3-domain of the 16S DNA sequence, and the domain-specific sequence of each primer of the reverse primer set is substantially complementary to the C5-domain of the 16S DNA sequence. These primers, in combination, would amplify the V4-V5 regions of the 16S DNA sequence.

In some embodiments, each primer in a composition disclosed herein has an at least partial adapter sequence, for facilitating sequencing of said sequence. In these embodiments, the composition can further include at least one pair of forward and reverse adapter oligonucleotide primers that are substantially complementary to the at least partial adapter sequence of the primers. This composition can further include at least one pair of forward and reverse universal oligonucleotide primers that are substantially complementary to the adapter oligonucleotide primers.

A specific embodiment provides: a first set of forward, overlapping primers, with the domain-specific sequence of each primer of the first forward primer set being substantially complementary to the C2-domain of a 16S DNA sequence; a second of forward, overlapping primers, with the domain-specific sequence of each primer of the second forward primer set being substantially complementary to the C3-domain of a 16S DNA sequence; a first set of reverse, overlapping primers, with the domain-specific sequence of each primer of the first reverse primer set being substantially complementary to the C4-domain of a 16S DNA sequence; and a second set of reverse, overlapping primers, with the domain-specific sequence of each primer of the second reverse primer set being substantially complementary to the C5-domain of a 16S DNA sequence. When these primers are used together in an amplification reaction, the frame-shifted amplicons generated include amplicons covering the V4 region, amplicons covering the V3 and V4 regions, amplicons covering the V4 and V5 regions, and amplicons covering the V3, V4, and V5 regions.

In another embodiment, a composition can include oligonucleotide primers with sequences selected from SEQ ID NO: 2 through SEQ ID NO: 20. Within this embodiment, a composition can include two or more oligonucleotide forward primers selected from SEQ ID NOS: 2, 3, 4, 5, 6, 7, 8, 16, and 17, and two or more oligonucleotide reverse primers selected from SEQ ID NOS: 9, 10, 11, 12, 13, 14, 15, 18, 19, and 20. Also within this embodiment, a composition can include two or more oligonucleotide forward primers selected from SEQ ID NOS: 2, 3, 4, 5, and 16, and two or more oligonucleotide reverse primers selected from SEQ ID NOS: 9, 10, 11, 12, 13, and 18, for amplification of V3 to V4 regions. Further within this embodiment, a composition can include two or more oligonucleotide forward primers selected from SEQ ID NOS: 6, 7, 8, and 17, and two or more oligonucleotide reverse primers selected from SEQ ID NOS: 14, 15, 19, and 20, for amplification of V4 to V5 regions.

Also disclosed herein are methods to identify a plurality of microorganisms in a sample. The methods include the steps of: (a) amplifying DNA from a sample with a forward primer set and a reverse primer set, each primer set having one or more oligonucleotide primers, and at least one set having multiple primers. Each primer within each set has a domain-specific sequence that is substantially complementary to a conserved domain of a bacterial or archaeal ribosomal 16S DNA sequence adjacent to the V3, V4, or V5 region of the 16S DNA sequence. For each primer set that includes multiple primers, the primers within the multiple primer set are overlapping primers which are substantially complementary to a single conserved domain, and each primer within the set differs from at least another primer within the set by a frame shift of one to three nucleotides at the 5' end of the domain-specific sequence, such that an amplification reaction using the forward primer set in combination with a reverse primer set generates frame-shifted amplicons. After amplification, the disclosed methods further include (b) isolating the generated frame-shifted amplicons from the amplified DNA, (c) sequencing the isolated amplicons, and (d) identifying the microorganisms present in the sample based on identification of species-specific 16S DNA sequences.

In the disclosed methods, each primer in a primer set with multiple primers can have at least one random nucleotide adjacent to the 5' start of the domain-specific sequence. Each primer in a primer set with multiple primers can also, or alternatively, have at least one degenerate nucleotide within the domain-specific sequence. In some embodiments, both the forward primer set and the reverse primer set in the method have multiple overlapping primers.

In one embodiment of the disclosed methods, the amplification step (a) involves use of four sets of primers: a first set of forward, overlapping primers, with the domain-specific sequence of each primer of the first forward primer set being substantially complementary to the C2-domain of a 16S DNA sequence; a second of forward, overlapping primers, with the domain-specific sequence of each primer of the second forward primer set being substantially complementary to the C3-domain of a 16S DNA sequence; a first set of reverse, overlapping primers, with the domain-specific sequence of each primer of the first reverse primer set being substantially complementary to the C4-domain of a 16S DNA sequence; and a second set of reverse, overlapping primers, with the domain-specific sequence of each primer of the second reverse primer set being substantially complementary to the C5-domain of a 16S DNA sequence. In the second step of the method, these primers are used together in an amplification reaction, to generate frame-shifted amplicons including amplicons covering the V4 region, amplicons covering the V3 and V4 regions, amplicons covering the V4 and V5 regions, and amplicons covering the V3, V4, and V5 regions.

In a specific embodiment of the above example, the amplification step (a) further includes the steps of (i) amplifying DNA from a portion of the sample using the first set of forward, overlapping primers and the first set of reverse, overlapping primers, to generate amplicons comprising the V3 and V4 regions; (ii) amplifying DNA from a different portion of the sample using the second set of forward, overlapping primers and the second set of reverse, overlapping primers to generate amplicons covering the V4 and V5 regions; (iii) pooling the reaction mixtures from steps (i) and (ii); and (iv) amplifying DNA in the pooled mixture to generate a library of frame-shifted amplicons which include amplicons covering the V3 and V4 regions, amplicons covering the V4 and V5 regions, amplicons covering the V4 region, and amplicons covering the V3, V4, and V5 regions.

In a further specific embodiment of the above method, each of the primers has an at least partial adapter sequence. In this embodiment, adapter primers and universal primers are added to the pooled reaction mixture of step (iii) prior to performing the DNA amplification in step (iv). In an additional specific embodiment, the DNA amplification in step (i) and (ii) includes eight to twelve cycles of PCR, and the DNA amplification in step (iv) includes five to seven cycles of PCR. In a final embodiment, the amplified DNA is sequenced using solid surface-based sequencing.

BRIEF DESCRIPTION OF THE FIGURES

FIGS. 5A-5B. Comparison of numbers of taxa identified using "old" method with new primers and methods disclosed herein for samples VX1344 (A) and VX1345 (B).

FIGS. 6A-6B. Comparison of numbers of taxa identified using "old" method with new primers and methods disclosed herein for samples VX1348 (A) and VX1349 (B).

FIGS. 7A-7B. Comparison of numbers of taxa identified using "old" method with new primers and methods disclosed herein for samples VX1346 (A) and VX1347 (B).

DETAILED DESCRIPTION OF THE DISCLOSURE

Disclosed herein are compositions that have uniquely designed oligonucleotide primers for identifying a plurality of microorganisms in a sample, and improved methods for detection of microbial populations from diverse types of samples.

A "sample" can be any sample that includes one or more species of microorganism, or any specimen for which elucidation of the microbial species in the specimen is desired. A sample can be a biological sample, such as a clinical specimen from a human or animal, or an environmental sample, such as a water, soil, air, structure, or equipment specimen.

As used herein, a "microorganism" or "microbe" includes, but is not limited to, a bacterium or *eubacterium*, an archaebacterium, a fungus, a protozoan and the like.

The disclosed methods and compositions are capable of distinguishing and differentiating among species of microorganism based on identification of species-specific 16S ribosomal DNA ("16S rDNA" or "16S DNA") sequences.

16S sequencing uses the *E. coli* 16S DNA sequence as a standard reference. The *E. coli* 16S RNA sequence is available as GenBank Accession No. J01859, and further provided herein as SEQ ID NO: 1.

```
                                                        SEQ ID NO: 1
AAAUUGAAGA GUUUGAUCAU GGCUCAGAUU GAACGCUGGC GGCAGGCCUA

ACACAUGCAA GUCGAACGGU AACAGGAAGC AGCUUGCUGC UUCGCUGACG

AGUGGCGGAC GGGUGAGUAA UGUCUGGGAA GCUGCCUGAU GGAGGGGAU

AACUACUGGA AACGGUAGCU AAUACCGCAU AAUGUCGCAA GACCAAAGAG

GGGGACCUUC GGGCCUCUUG CCAUCGGAUG UGCCCAGAUG GGAUUAGCUU

GUUGGUGGGG UAACGGCUCA CCAAGGCGAC GAUCCCUAGC UGGUCUGAGA

GGAUGACCAG CCACACUGGA ACUGAGACAC GGUCCAGACU CCUACGGGAG

GCAGCAGUGG GGAAUAUUGC ACAAUGGGCG CAAGCCUGAU GCAGCCAUGC

CGCGUGUAUG AAGAAGGCCU UCGGGUUGUA AAGUACUUUC AGCGGGGAGG

AAGGGAGUAA AGUUAAUACC UUUGCUCAUU GACGUUACCC GCAGAAGAAG

CACCGGCUAA CUCCGUGCCA GCAGCCGCGG UAAUACGGAG GGUGCAAGCG

UUAAUCGGAA UUACUGGGCG UAAAGCGCAC GCAGGCGGUU UGUUAAGUCA

GAUGUGAAAU CCCCGGGCUC AACCUGGGAA CUGCAUCUGA UACUGGCAAG

CUUGAGUCUC GUAGAGGGGG GUAGAAUUCC AGGUGUAGCG GUGAAAUGCG

UAGAGAUCUG GAGGAAUACC GGUGGCGAAG GCGGCCCCCU GGACGAAGAC

UGACGCUCAG GUGCGAAAGC GUGGGGAGCA AACAGGAUUA GAUACCCUGG

UAGUCCACGC CGUAAACGAU GUCGACUUGG AGGUUGUGCC CUUGAGGCGU

GGCUUCCGGA GCUAACGCGU UAAGUCGACC GCCUGGGGAG UACGGCCGCA

AGGUUAAAAC UCAAAUGAAU UGACGGGGGC CCGCACAAGC GGUGGAGCAU

GUGGUUUAAU UCGAUGCAAC GCGAAGAACC UUACCUGGUC UUGACAUCCA

CGGAAGUUUU CAGAGAUGAG AAUGUGCCUU CGGGAACCGU GAGACAGGUG

CUGCAUGGCU GUCGUCAGCU CGUGUUGUGA AAUGUUGGGU UAAGUCCCGC

AACGAGCGCA ACCCUUAUCC UUUGUUGCCA GCGGUCCGGC CGGGAACUCA

AAGGAGACUG CCAGUGAUAA ACUGGAGGAA GGUGGGGAUG ACGUCAAGUC

AUCAUGGCCC UUACGACCAG GGCUACACAC GUGCUACAAU GGCGCAUACA

AAGAGAAGCG ACCUCGCGAG AGCAAGCGGA CCUCAUAAAG UGCGUCGUAG

UCCGAUUGG AGUCUGCAAC UCGACUCCAU GAAGUCGGAA UCGCUAGUAA

UCGUGGAUCA GAAUGCCACG GUGAAUACGU UCCCGGGCCU UGUACACACC

GCCCGUCACA CCAUGGGAGU GGGUUGCAAA AGAAGUAGGU AGCUUAACCU
```

```
UCGGGAGGGC GCUUACCACU UUGUGAUUCA UGACUGGGGU GAAGUCGUAA

CAAGGUAACC GUAGGGGAAC CUGCGGUUGG AUCACCUCCU UA
```

Figure 1:
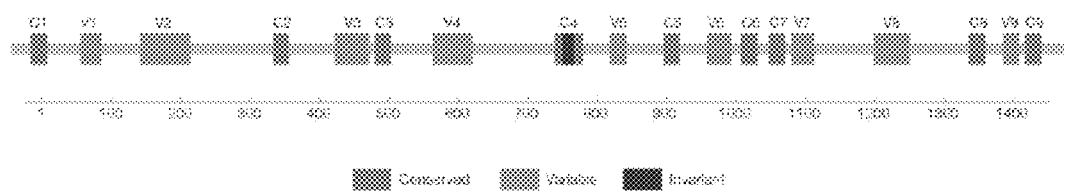
FIG. 1. Diagram of conserved and variable domains of 16S rDNA.

16S bacterial DNA sequences contain regions of high conservation across taxa ("conserved" regions or domains) alternating with regions of low conservation across taxa ("variable" or "hypervariable" regions or domains). FIG. 1 illustrates the organization of conserved ("C") domains and variable ("V") domains along the length of the 16S DNA sequence. 16S DNA variable/hypervariable ("V") domains fall approximately along the *E. coli* sequence/SEQ ID NO: 1 as follows: positions 68-100 ("V1"), 137-226 ("V2"), 440-496 ("V3"), 590-651 ("V4"), 829-856 ("V5"), 1000-1036 ("V6"), 1119-1156 ("V7"), 1244-1295 ("V8"), and 1435-1465 ("V9").

Conserved ("C") regions fall outside of the variable/V regions as follows: approximately at positions 1-67 ("C1"), 227-439 ("C2"), 497-589 ("C3"), 652-828 ("C4"), 857-999 ("C5"), 1037-1118 ("C6"), 1157-1243 ("C7"), 1296-1434 ("C8"), and 1466-1542 ("C9"). The following regions are highly conserved across eubacteria: positions at approximately 104-120, 314-368, 505-539, 683-707, 764-806, 879-893, 909-940, 949-964, 969-985, 1048-1114, and 1177-1197 corresponding to the *E. coli* 16S sequence. The following regions are highly conserved across archaebacteria: positions at approximately 344-367, 506-547, 779-806, 882-936, 947-973, 1043-1073, 1094-1111, and 1225-1242 corresponding to the *E. coli* 16S sequence (for review, see Wang et al., *PLOS ONE* 4:e7401 (2009)).

The prevalent strategy for sequencing microorganisms in a sample involves designing probes and primers that anneal to conserved regions at the edges of variable domains, for amplification and sequencing across variable domains to identify species-specific variable sequences and thus identify species within the sample. Typically, primer pairs have been designed to amplify a single variable region, such as the V3, V4, or V5 region. In addition, a single primer pair is typically used per amplification reaction.

The invention disclosed herein provides compositions, uniquely designed primers and primer sets, and PCR strategies to provide improved sensitivity and specificity, based on sequencing of a single V or across multiple V regions. The primers are designed for use in amplification reactions to generate amplicons containing one or more V regions of the 16S DNA. The primers and primer sets have features including one or more of: the ability to create frame-shifted amplicons; presence of degenerate nucleotides within the domain-specific sequence, and presence of random nucleotides adjacent to the start of the domain-specific sequence. The methods involve use of the disclosed primers and primer sets, preferably for high-throughput sequencing and identification of microorganisms in a sample.

Oligonucleotide Primer Compositions

Disclosed herein are compositions with a forward primer set and a reverse primer set for identifying microorganisms in a sample. Each primer in the composition has a domain-specific sequence that is substantially complementary to a conserved domain of a bacterial or archaeal ribosomal 16S DNA sequence adjacent to the V3, V4, or V5 region of the 16S DNA sequence. Each primer set has one or more primers, and at least one set has multiple primers. For each primer set that has multiple primers, the primers within the set are overlapping primers which are substantially complementary to a particular conserved domain, where each primer within the set differs from at least one other primer within the set by a frame shift of one to three nucleotides at the 5' end of the domain-specific sequence, such that, when the forward primer set and the reverse primer set are utilized in a nucleic acid amplification reaction, frame-shifted amplicons can be generated.

As used herein, a "primer" is an oligonucleotide that is capable of annealing to a target nucleic acid sequence and serves as a starting point for DNA synthesis/amplification. Primers may or may not contain additional features (e.g., a fluorescent moiety, a dye, a bead, a particle, a nucleic acid sequence, etc) which allow for detection, immobilization, or manipulation of the target nucleic acid sequence. A "primer set" is a collection of one, two, three, or more oligonucleotides designed to anneal to a given sequence in either the forward (5'-3') or reverse (3'-5') direction of the nucleic acid strand. Methods for preparation of labeled DNA and RNA probes and primers, and the conditions for annealing thereof to a target nucleic acid sequence, are described in Molecular Cloning: A Laboratory Manual, J. Sambrook et al., eds., 2nd edition (Cold Spring Harbor Laboratory Press, 1989), Chapters 10 and 11, the disclosures of which are incorporated herein by reference.

Compositions disclosed herein include at least a first set of forward primers, and a first set of reverse primers. As noted above, "forward" primers are designed to amplify nucleic acid sequences in the 5' to 3' direction, while "reverse" primers are designed to amplify nucleic acid sequences in the 3' to 5' direction. A set of forward primers is paired with a set of reverse primers for amplification of a given target sequence. A nucleic acid "copy" generated by amplification is referred to herein as an "amplicon". Each primer set has one or more oligonucleotide primers, such as 1, 2, 3, 4, 5, 8, 10, 12, 15, 18, 20, 25, or more primers, or 1-5, 6-10, 11-15, 16-20, 21-25, 26-30, 31-35, 36-40, 41-45, 46-50, or 50 or more primers. At least one of the forward or reverse primer sets has multiple primers. In some embodiments, both forward and reverse primer sets have multiple primers.

Each primer disclosed herein has a domain-specific sequence that is substantially complementary to a conserved domain of a eubacterial and/or archaeal ribosomal 16S DNA sequence. The domain-specific sequence is a stretch of preferably 10-50, more preferably 15-35, and most preferably 15-30 nucleotides, that anneals to a conserved domain with substantial complementarity. An oligonucleotide primer is "complementary" to a target nucleotide sequence when the primer can anneal (that is, base pair, or form Watson-Crick hydrogen bonds) with the target nucleotide sequence. An oligonucleotide is "substantially complementary" to a target nucleotide sequence when it anneals with the target sequence under stringent annealing conditions. By "substantially complementary" is also meant that the disclosed primers have at least about 70%, 75%, 80%, 85%, 90%, 95%, 98% or 99% identity to a domain-specific sequence, as well as primers that have complete identity to a domain-specific sequence. Because even conserved regions show some variation between species, the complementarity may be in relation to a conserved domain of the *E.*

*coli* reference genome, or in relation to a conserved domain adjacent to a variable region of interest in another microbial species 16S DNA.

The term "stringent annealing conditions" is defined as conditions under which a nucleotide sequence anneals specifically with a target sequence(s) and not with non-target sequences, as can be determined empirically. The term "stringent conditions" is functionally defined with regard to the annealing of a nucleic-acid primer to a target nucleic acid (i.e., to a particular nucleic acid sequence of interest) by the specific annealing procedures discussed in Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985).

Whether a primer can anneal only to its perfect complement or also to sequences that have one or more mismatches, depends in large part upon the annealing temperature. The annealing temperature is also referred to as the melting temperature ($T_m$), the temperature at which one-half of a particular DNA duplex will dissociate into single stranded DNA. The stability of a primer-template DNA duplex can be measured by its $T_m$. Primer length and sequence are of critical importance in designing the parameters of a successful amplification. The melting temperature of a nucleic acid duplex increases both with its length, and with increasing GC content. A formula for calculation of the ($T_m$), where N is the number of nucleotides in the primer, is presented as Formula 1:

$$T_m = 64.9° C. + 41° C. \times (\text{number of } G\text{'s and } C\text{'s in the primer} - 16.4)/N$$

In addition to annealing temperature, salt concentration ($Na^+$, $K^+$, and particularly $Mg^{++}$) and other additives such as DMSO, betaine and glycerol also affect primer annealing specificity. PCR is typically performed in the presence of ~50 mM monovalent cations. A formula for calculating $T_m$ that includes ionic conditions, is presented as Formula 2:

$$T_m = 81.5° C. + 16.6° C. \times (\log_{10}[Na^+] + [K^+] + [Mg^{++}]) + 0.41° C. \times (\% GC) - 675/N$$

In general, the higher the annealing temperature, the more specific annealing of the primer to its perfect matched template and so the greater the likelihood of only target sequence amplification can be accomplished. The lower the temperature, the more mismatches between template and primer can be tolerated, leading to increased amplification of non-target sequences. Primers with melting temperatures above 50° C. are generally preferred over primers with lower melting temperatures. As disclosed herein, stringent annealing conditions involve annealing temperatures ranging from about 50° C. to 72° C., preferably 53° C. to 63° C., even more preferably 55-60° C.

The domain-specific sequence is complementary to a conserved domain adjacent to the V3, V4, or V5 region of a 16S DNA sequence. By "adjacent" is meant that the conserved domain abuts, or is located within 10, 20, 30, 40, 50, or 60 nucleotides from the variable region of interest. The conserved domain can be located 5' or 3' relative to the V region of interest. For example, the conserved domains adjacent to V4 are at approximate positions 497-589, including conserved domain C3 (5' to the V4 region) and positions 652-828, including conserved domain C4 (3' to the V4 region). Similarly, the conserved domains adjacent to V3 are at approximate positions 227-439, including conserved domain C2 (5' to the V3 region) and positions 497-589, including conserved domain C3 (3' to the V3 region). The conserved domains adjacent to V5 are at approximate positions 652-828, including conserved domain C4 (5' to the V5 region) and positions 857-999, including conserved domain C5 (3' to the V5 region). Primers can be substantially complementary to any position within a conserved domain that allows amplification of the variable region of interest. In one embodiment, primers are substantially complementary to a highly conserved region or a portion of a highly conserved region, such as the highly conserved regions at positions 515-535 in C3, 781-806 in C4, or 907-939 in C5.

For each primer set that has multiple primers, the primers within the set are overlapping primers, meaning each primer within the set differs from at least one other primer within the set by a frame shift of one to three nucleotides at the 5' end of the domain-specific sequence, such that frame-shifted amplicons (amplified sequences) can be generated in an amplification reaction. The inventors have found that the presence of multiple overlapping primers in an amplification reaction improves both the sensitivity and specificity of microorganism detection.

An "overlap" or "frame shift" between primers means that the domain-specific sequence of one primer is "shifted" by at least one or two nucleotides at the 5' start of the domain-specific sequence, relative to the 5' start of the domain-specific sequence of another primer. Overlapping primers anneal to the same region/domain, but the target sequence is shifted between the primers towards the 3' by one or more nucleotides. Thus, for a stretch of nucleotides "ATCG CC . . . ", one primer could start with "ATCG . . . ", while an overlapping primer could start "CGCG . . . ". Accordingly, overlapping primers can differ by a shift of 1, 2, 3, 4, 5, 6, 7, 8, 9, 10, 11, or 12 nucleotides along the length of a target domain-specific sequence.

In some embodiments, when there are 2 primers in a set, the two primers differ at the 5' end by a frame shift of 1, 2, 3, or 4 nucleotides. When there are more than 2 primers, the shift is serial and there can be 4 or more nucleotides (e.g., 4, 5, 6, 7, 8, 9, or 10 or more nucleotides) shifted when comparing the last primer relative to the first primer in the set. Specific examples of frame-shifted primers include primers that bind to the 16S sequence at approximate starting positions 341, 343, 347, and 349; 515, 517, and 519; 802, 803, 805, and 806; and 926, 934 and 939.

Frame-shifted primers generate, in an amplification reaction, frame-shifted amplicons which differ by 1 or more nucleotides at the 5' end. The use of frame-shifted primers enables improved detection of multiple species by increasing the chances of annealing to a less-conserved sequence. In addition, frame-shifted amplicons provide better resolution for sequencing using next generation sequencing methods.

Overlapping primers increases the detection of many different microbes. The nucleotide sequence of conserved domains of the 16S DNA varies between microorganisms, such that no single primer designed to anneal to conserved domain can anneal to that conserved domain in every species. For any given consensus sequence, some microbial sequences will have more conservation of one portion of the consensus sequence, while other microbial sequences can show more conservation of a different portion of the consensus sequence. Thus, the presence of two or more primers that anneal slightly upstream or downstream from one another, separated by a few nucleotides of sequence, improves the odds of annealing to many conserved domains of varying sequence, thus increasing the sensitivity and specificity of detection of multiple different species.

The use of overlapping primers creates frame-shifted amplicons. These amplicons differ at the 5' end by only a few nucleotides, but this shift increases the diversity of the amplicon library, improves disambiguated identification of adjacent clusters, and improves sequencing using high throughput sequencing technologies (such as the sequencing platform of Illumina, Inc.) which relies on fluorescent image for base calling.

The disclosed compositions, primers, and methods generate nucleic acid sequences which can be sequenced by any method known in the art. For example, traditional sequencing methods such as Sanger sequencing, or next generation sequencing methods, are all suitable for sequencing the amplicons generated by the primer compositions and methods disclosed herein. However, given the potentially large number and variety of microorganisms which can be present in a given sample, high-throughput/next generation sequencing methods, which are capable of rapidly generating large amounts of sequence data, are considered better suited for the rapid and accurate identification of microorganisms in a sample. "Next generation" sequencing technologies enable a large number of distinct nucleic acid sequences to be sequenced simultaneously and at a high density, including, but not limited to, sequencing-by-synthesis (e.g., Illumina dye sequencing; Single Molecule Real Time Sequencing platform by Pacific Biosciences); sequencing by ligation (SOLiD or Polony sequencing platform, Applied Biosystems); pyrosequencing (454 Sequencing, Roche Diagnostics); and ion semiconductor sequencing (Ion Torrent Sequencing, Life Technologies).

A preferred sequencing technology is solid-phase nucleic acid amplification such as the sequencing-by-synthesis method, as exemplified by the Illumina sequencing technology. In this method, DNA library fragments are first amplified to form clusters of identical single strand DNA fragments on a glass slide, prior to sequencing. Reversibly labeled fluorescent dNTPs are incorporated by DNA polymerase onto the primers annealing to the ssDNA library, extending by one base at a time. The nucleotide's fluorescence is imaged by the Illumina HiSeq or MiSeq platform (that is, read as being incorporated) and then enzymatically cleaved off to allow for incorporation of the next nucleotide. Each cluster is base-called based on the fluorescent image.

One challenge faced by solid support-based/DNA colony sequencing methods, such as Illumina, is that the cluster calling software (the software that distinguishes one colony from another) relies on a diversity of DNA fragments to differentiate between clusters; the software needs variation in sequences to disambiguate adjacent clusters and identify multiple sequences. A shortage of diversity is frequently encountered when libraries are of amplicons generated with simple primer pairs. To circumvent the problem, standard methodologies recommend the addition or "spike in" of control DNA to artificially increase fragment diversity. The amount of the control DNA has to be decided empirically and one can end up burning 40% of the total reads on the control genome, which provides no data on the actual sequences of interest.

The inventors have found that, not only does the use of multiple, overlapping primers provide improved taxonomic coverage of microbial species in a sample, but the plurality of frame-shifted amplicons generated with these methods also introduces high complexity to the sequencing library, compared to amplicons generated by amplification from a single primer pair. In this case, the fluorescence emitted differs between two otherwise similar sequences, because of the shifted priming sites. Thus, the primers provided herein allow for high-quality sequencing without the use of spike-in DNA. Without spiking-in control DNA, nearly twice as many samples can be sequenced. In this way, the use of overlapping primers increases the sensitivity and specificity of microorganism detection; increases the diversity of sequences for high-throughput sequencing; and increases the total number of sequences that can be read in a sequencing run, by enabling high-quality sequencing without the need for spike-in control DNA.

The disclosed primers can also include at least one random nucleotide adjacent to the 5' start of the domain-specific sequence, to provide additional improvements on sensitivity and specificity. A "random" nucleotide is any of A, T, C, or G, at a specified position (also referred to as "N" or "n" in Table 1). By "adjacent to the 5' start of the domain-specific sequence" is meant that the random nucleotide is at a position immediately 5' to, or within 1, 2, 3, 4, or 5 nucleotides of, the first nucleotide of the domain-specific sequence. In some embodiments, a primer has one random nucleotide adjacent to the 5' start of the domain-specific sequence. In other embodiments, a primer has 2, 3, or 4 random nucleotides adjacent to the 5' start of the domain-specific sequence. Within each set, preferably, primers sharing a common domain-specific sequence have an identical number of random nucleotides at the same position(s) adjacent to the 5' start of the domain-specific sequence. The addition of at least one random nucleotide adjacent to the 5' start of the primer domain-specific sequence further increases the potential for annealing to many different microbial 16S sequences, thus improving detection of the total numbers and types of species present in the sample. The presence of a random nucleotide or nucleotides also further increases library complexity for high-throughput sequencing.

In other embodiments, each primer in a primer set as disclosed herein can include at least one degenerate nucleotide within the domain-specific sequence. A "degenerate" nucleotide indicates that several different alternative nucleotides may be present at the position of degeneracy. The inventors have identified certain positions within the conserved domains that show variation in sequence between different species. Therefore, the disclosed primers can include degenerate nucleotides at positions that are associated with variation among species, to increase the ability of the primer pool to anneal to the sequences of many divergent species.

The standard nucleotide bases are A, C, G, T. Nucleotides at degenerate positions can vary, for example, a sequence with a degenerate nucleotide can have an "R" at a particular position (meaning the sequence can have an A or G at that position), a "Y" at a particular position (meaning the sequence can have a C or T at that position), a "V" at a particular position (meaning the sequence can have an a C, G, or A at that position), or an "N" at a particular position (meaning the sequence can have an any of the four bases at that position), relative to the sequence of another primer containing the same domain-specific sequence. Thus, for example, the sequence "GYG" indicates that the sequence can be either "GCG" or "GTG". The standard nucleotide IUPAC code is provided in Table 1. In some embodiments, a primer has a degenerate nucleotide at one, two, three, four, or five or more positions. In some further embodiments, the primer has two or more degenerate nucleotides adjacent to each other.

TABLE 1

IUPAC nucleotide code.

| IUPAC nucleotide code | Base |
|---|---|
| A | Adenine |
| C | Cytosine |
| G | Guanine |
| T (or U) | Thymine (or Uracil) |
| R | A or G |
| Y | C or T |
| S | G or C |
| W | A or T |
| K | G or T |
| M | A or C |
| B | C or G or T |
| D | A or G or T |
| H | A or C or T |
| V | A or C or G |
| N or n | any base |

Degenerate nucleotides are placed at positions showing divergent nucleotide use across species, and are preferably limited to the nucleotides which occur most frequently at those positions. Specific positions of degeneracy/variability in conserved domains identified by the inventors and incorporated into the disclosed primer sets, and the degenerate nucleotide incorporated according to Table 1, includes positions 348 (R), 349 (R), 350 (Y), 354 (S), 358 (K), 359 (R), 360 (R), 361 (M), 518 (Y), 523 (M), 793 (W), 798 (R or V), 799 (N or H), 912 (R), 916 (M), and 917 (Y) of SEQ ID NO: 1.

A forward or reverse primer set can include a single primer, or can include multiple primers. Where a set has two or more primers, the primers can differ by a frame-shift between the domain-specific sequence of the two primers. Two or more primers can also, or alternatively, differ by the presence of at least one different random nucleotide adjacent to the 5' start of the domain-specific sequence. Two or more primers can also, or alternatively, differ by the presence of at least one different degenerate nucleotide within the domain-specific sequence.

When one set of forward and one set of reverse primers are used, preferably these are designed to amplify a region containing all or part of the V3, V4, or V5 regions, most preferably containing at least a part of the V4 region. When more amplicons, or amplicons containing more than one V region, are desired, additional sets of forward and/or reverse primers can be used. For example, sets of forward and reverse primers can be used to generate amplicons containing the V3 and V4 regions (V3-V4 amplicons); the V4 and V5 regions (V4-V5 amplicons); the V3, V4, and V5 regions (V3-V4-V5 amplicons); and combinations of amplicons including V3-V4 amplicons, V4-V5 amplicons, and V3-V4-V5 amplicons. The amplicons desired to be generated drives the selection of primers utilized in the composition.

In a specific embodiment, two sets of forward, overlapping primers and two sets of reverse, overlapping primers are provided. In this embodiment, the domain-specific sequence of each primer of the first forward primer set is substantially complementary to the C2-domain of a 16S bacterial DNA sequence; and the domain-specific sequence of each primer of the second forward primer set is substantially complementary to the C3-domain of a 16S bacterial DNA sequence. Also in this embodiment, the domain-specific sequence of each primer of the first reverse primer set is substantially complementary to the C4-domain of a 16S bacterial DNA sequence; and the domain-specific sequence of each primer of the second reverse primer set is substantially complementary to the C5-domain of a 16S bacterial DNA sequence. When these primer sets are used together in an amplification reaction, frame-shifted amplicons are generated including V4 amplicons, V3-V4 amplicons, V4-V5 amplicons, and V3-V4-V5 amplicons.

In some embodiments, a primer sequence as disclosed herein includes an adapter or partial adapter sequence so that the generated amplicon can be utilized for high-throughput sequencing, such as solid surface-based sequencing. An "adapter sequence" is a sequence designed to anneal the amplicon to surface-bound nucleotides, which anchor the amplicon to the surface for automated sequencing. A "partial adapter sequence" is complementary to a portion of an adapter primer, in situations where the adapter primer itself provides the sequence of the amplicon which anneals to surface-bound nucleotides for anchoring to a solid surface. An example of a partial adapter sequence that can be designed into a forward primer is 5'-ACACTCTTTCCCTA-CACGACGCTCTTCCGATCT (SEQ ID NO: 21). An example of a partial adapter sequence that can be designed into a reverse primer is 5'-GACTGGAGTTCAGACGTGT-GCTCTTCCGATCT (SEQ ID NO: 22).

Exemplary primer sequences provided herein are listed below. These primers include a partial adapter sequence, and a random nucleotide ("n") or two random nucleotides ("nn"), followed by the domain-specific sequence. Theses primers further include one or more degenerate nucleotide within the domain-specific sequence.

```
U341F-p5
                                        (SEQ ID NO: 2)
ACACTCTTTCCCTACACGACGCTCTTCCGATCTnCCTACGGGRSGCAGCA

E343F-p5
                                        (SEQ ID NO: 3)
ACACTCTTTCCCTACACGACGCTCTTCCGATCTnTACGGRAGGCAGCAG

E347F-p5
                                        (SEQ ID NO: 4)
ACACTCTTTCCCTACACGACGCTCTTCCGATCTnGGAGGCAGCAGTRRGG
AAT

A349F-p5
                                        (SEQ ID NO: 5)
ACACTCTTTCCCTACACGACGCTCTTCCGATCTnGYGCASCAGKCGMGAA

U515F-p5
                                        (SEQ ID NO: 6)
ACACTCTTTCCCTACACGACGCTCTTCCGATCTnGTGYCAGCMGCCGCGG
TAA

E517F-p5
                                        (SEQ ID NO: 7)
ACACTCTTTCCCTACACGACGCTCTTCCGATCTnGCCAGCAGCCGCGGTA
A

A519F-p5
                                        (SEQ ID NO: 8)
ACACTCTTTCCCTACACGACGCTCTTCCGATCTnCAGCMGCCGCGGTAA

E802R-p7
                                        (SEQ ID NO: 9)
GACTGGAGTTCAGACGTGTGCTCTTCCGATCTnTACNVGGGTATCTAATCC

E802R-p7
                                        (SEQ ID NO: 9)
GACTGGAGTTCAGACGTGTGCTCTTCCGATCTnTACNVGGGTATCTAATC
C
```

-continued

E803R-p7
(SEQ ID NO: 10)
GACTGGAGTTCAGACGTGTGCTCTTCCGATCTnCTACCRGGGTATCTAATCC

E806R-p7
(SEQ ID NO: 11)
GACTGGAGTTCAGACGTGTGCTCTTCCGATCTnGGACTACHVGGGTWTCTAAT

U805R-p7
(SEQ ID NO: 12)
GACTGGAGTTCAGACGTGTGCTCTTCCGATCTnGACTACHVGGGTATCTAATCC

A806R-p7
(SEQ ID NO: 13)
GACTGGAGTTCAGACGTGTGCTCTTCCGATCTnGGACTACVSGGGTATCTAAT

E939R-p7
(SEQ ID NO: 14)
GACTGGAGTTCAGACGTGTGCTCTTCCGATCTnCTTGTGCGGGCCCCGTCAATTC

A934R-p7
(SEQ ID NO: 15)
GACTGGAGTTCAGACGTGTGCTCTTCCGATCTnTCCCCCGCCAATTCCTTTAA

E347F-p5-n
(SEQ ID NO: 16)
ACACTCTTTCCCTACACGACGCTCTTCCGATCTnnGGAGGCAGCAGTRRGGAAT

U515F-p5-n
(SEQ ID NO: 17)
ACACTCTTTCCCTACACGACGCTCTTCCGATCTnnGTGYCAGCMGCCGCGGTAA

U805R-p7-n
(SEQ ID NO: 18)
GACTGGAGTTCAGACGTGTGCTCTTCCGATCTnnGACTACHVGGGTATCTAATCC

E939R-p7-n
(SEQ ID NO: 19)
GACTGGAGTTCAGACGTGTGCTCTTCCGATCTnnCTTGTGCGGGCCCCGTCAATTC

BE926R-p7
(SEQ ID NO: 20)
GACTGGAGTTCAGACGTGTGCTCTTCCGATCTnCCGTCAATTYMTTTRAGTtt

Compositions of the invention can further include, in addition to primers for amplification of target 16S sequences, adapter primers and universal primers for arraying and identifying sequences for high-throughput sequencing, particularly solid surface-based sequencing. Adapter primers and universal primers are particularly utilized where the primers of the invention contain a partial adapter sequence. Universal primers and adapter primers are one method to enable the binding of amplicons to a flow cell for next generation sequencing, allow for PCR enrichment of adapter-ligated DNA fragments only, and allow for indexing or "barcoding" of samples so multiple DNA libraries can be mixed together into 1 sequencing lane (known as multiplexing).

Adapter primers (also referred to as "indexed adapters") provide a "barcode" for sequence identification, and have a short sequence of complementarity to universal primers. Adapter primers can contain barcodes in one direction (forward or reverse only) or both directions (forward and reverse). Both single-directional barcodes or bi-directional barcodes can be utilized with the disclosed primers. Adapter primers in one direction with 1-20, preferably 8-18, more preferably 8, 9, 10, 11, 12, 13, 14, 15, or 16 distinct barcodes, and reverse adapter primers with 1-20, preferably 1-16, most preferably 1-12 distinct barcodes, are used. In a specific example, forward adapter primers with 12 distinct barcodes, and reverse adapter primers with 8 distinct barcodes, providing 20 distinct barcodes in total, can be utilized to generate 96 distinct barcoded sequences (12 times 8 equals 96) for use in multiplexed libraries. Similarly, forward adapter primers with 8 distinct barcodes, and reverse adapter primers with 12 distinct barcodes, providing 20 distinct barcodes in total, can also be utilized to generate 96 distinct barcoded sequences for use in multiplexed libraries.

Figure 3:
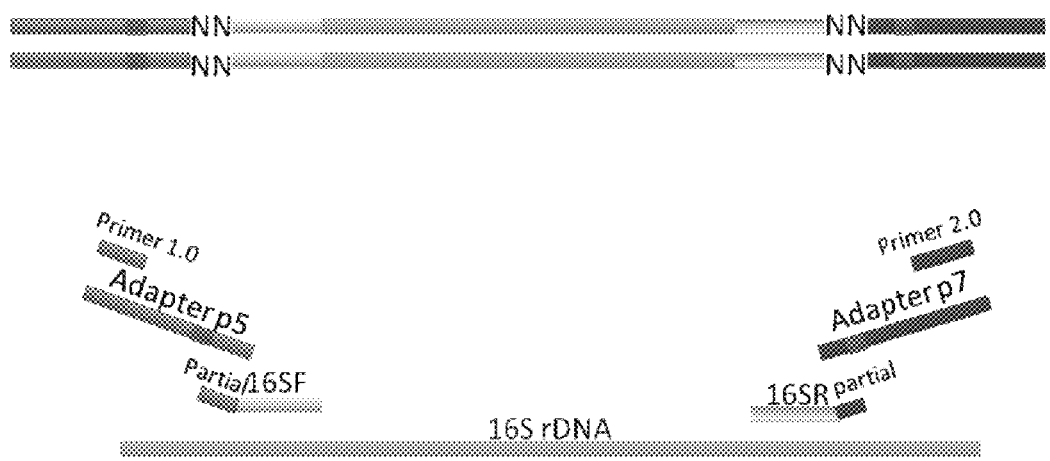
FIG. 3. Design for amplicon generation using gene-specific primers, adapter primers, and universal primers.
Figure 4:
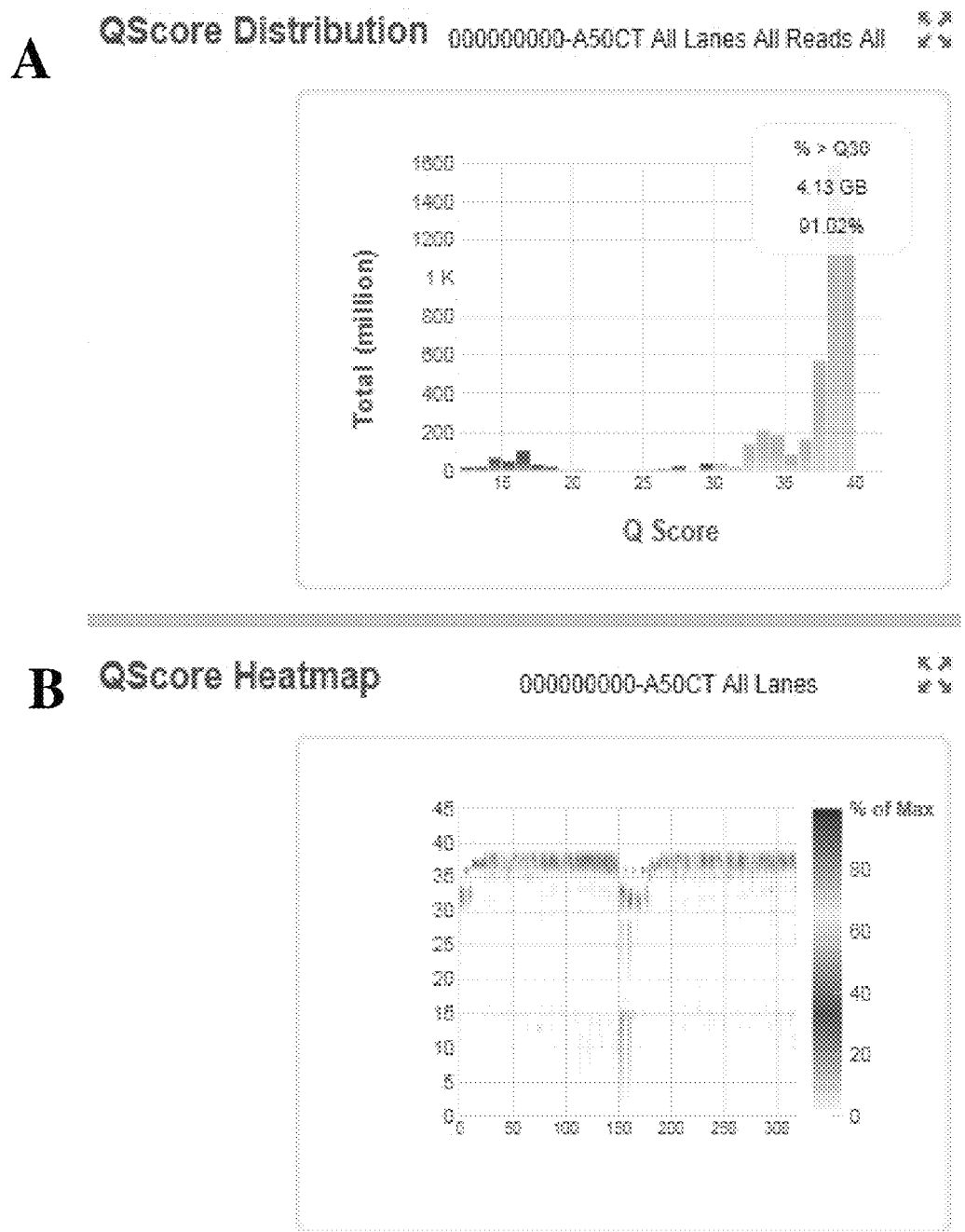
FIGS. 4A-4D. (A, C) Amplicons generated using primers of the invention and sequenced by solid support-based high throughput sequencing without using PhiX control DNA. (B, D) Amplicons generated using old method and sequenced by solid support-based high throughput sequencing with use of PhiX control DNA. A and B show QScore distribution showing number of reads with low error (less than 1 error per $10^3$ or 1000 bases). C and D show heatmaps indicating sequencing data quality. In all cases, quality of sequencing data was comparable between amplicons generated with new primers and methods, but without the need to waste sequencing reads on control DNA, relative to amplicons generated with prior art primers and methods and sequenced with spike-in PhiX control DNA.

Universal primers and adapter primers provide the sequence for binding to/anchoring single-stranded amplicons to a solid surface for arraying and sequencing. As seen in FIG. 3, adapter primers bind to the partial adapter sequences, while the universal primers (short pieces) facilitate this process, binding to the full length adapters. Specific adapter primers which can be used in the disclosed methods are commercially available, for example, from Illumina, Inc. and Life Technologies, Inc.

In specific embodiments, the compositions disclosed herein include oligonucleotide primers selected from the group consisting of SEQ ID NO: 2 through SEQ ID NO: 20. In further specific embodiments, the compositions disclosed herein include two or more oligonucleotide forward primers selected from SEQ ID NOS: 2, 3, 4, 5, 6, 7, 8, 16, and 17, and two or more oligonucleotide reverse primers selected from SEQ ID NOS: 9, 10, 11, 12, 13, 14, 15, 18, 19, and 20. In further specific embodiments, the compositions disclosed herein include two or more oligonucleotide forward primers selected from SEQ ID NOS: 2, 3, 4, 5, and 16, and two or more oligonucleotide reverse primers selected from SEQ ID NOS: 9, 10, 11, 12, 13, and 18, for amplification of V3 to V4 regions. In further specific embodiments, the compositions disclosed herein include two or more oligonucleotide forward primers selected from SEQ ID NOS: 6, 7, 8, and 17, and two or more oligonucleotide reverse primers selected from SEQ ID NOS: 14, 15, 19, and 20, for amplification of V4 to V5 regions.

The methods and compositions of the present invention can be conveniently packaged in kit form. Such kits can be used for the detection of microorganisms in an environmental or biological sample. A wide variety of kits may be prepared according to present invention. For example, a kit may include at least one forward primer set and at least one reverse primer set according to the invention; and instructional materials for utilizing the primer sets to amplify DNA from a sample for the determination of microorganisms in the sample. In addition, or alternatively, the kit can include reagents for DNA amplification. For example, the kit may include one or more of: a DNA or RNA polymerase; a reverse transcriptase; a DNA ligase; dNTP mix (e.g., dATP, dCTP, dGTP, dTTP); NTP mix (e.g., ATP, CTP, GTP, UTP); GC enhancer; labeled nucleotides; reaction buffers; salts;

nuclease-free water; and/or containers, vials, reaction tubes, and the like compatible with the methods of the present invention.

Detection Methods

This disclosure further provides methods to identify a plurality of microorganisms in a sample. The first step of the method involves amplifying DNA from a sample containing microorganisms, using a forward primer set and a reverse primer set to amplify 16S DNA from the microorganisms in the sample. The forward and reverse primer sets each have one or more oligonucleotide primers, with one or both sets including multiple primers. Each primer in each set has a domain-specific sequence that is substantially complementary to a conserved domain of a bacterial or archaeal ribosomal 16S DNA sequence adjacent to the V3, V4, or V5 region of the 16S DNA sequence. For each set that has multiple primers, the primers within the set are overlapping primers which are substantially complementary to the same conserved domain, and each primer within the set differs from at least another primer within the set by a frame shift of one to three nucleotides at the 5' end of the domain-specific sequence, such that the forward primer set and the reverse primer set generate frame-shifted amplicons in a nucleic acid amplification reaction.

A number of template dependent processes are available to amplify the marker sequences present in a given nucleic acid sample. One of the best known amplification methods is the polymerase chain reaction (referred to as PCR). Other methods of amplification are ligase chain reaction (LCR), Qbeta Replicase, isothermal amplification, strand displacement amplification (SDA), PCR-like template- and enzyme-dependent synthesis using primers with a capture or detector moiety, transcription-based amplification systems (TAS), cyclical synthesis of single-stranded and double-stranded DNA, "RACE", one-sided PCR, and di-oligonucleotide amplification.

The PCR method is well known in the art and disclosed, for example, in WO 99/28500; Sambrook et al. (*Molecular Cloning, A Laboratory Manual*, Cold Spring Harbor Laboratory Press, Cold Spring Harbor, N.Y. (2001)); *Nucleic Acid Hybridization* (Hames and Higgins eds., 1984); and *Current Protocols in Human Genetics* (Dracopoli et al., eds, 1984 with quarterly updates, John Wiley & Sons, Inc.), all of which are incorporated herein by reference. The PCR method utilizes a pair of oligonucleotide primers, each annealing to one strand of a double-stranded DNA/RNA template target. The primers flank the region that will be amplified. The PCR method comprises contacting the primers and target sequence, or mixture of target sequences and optional polynucleotide probes, and performing a series of repeated amplification steps of annealing the primers to the template, allowing DNA polymerase to "copy" the template strand starting from the primer sequence, separating the template strand from the primers and amplicons, and repeating the steps, until a sufficient number of amplicons is generated.

Once the amplification is completed, frame-shifted amplicons are isolated from the amplified DNA and sequenced. Microorganisms present in the sample are then identified based on identification of species-specific 16S DNA sequences in the amplicons generated from the sample.

In the disclosed methods, one or both of the forward and reverse primer sets has multiple, overlapping primers. As discussed above, the use of overlapping primers generates frame-shifted amplicons which improves detection of microorganisms, and also increases library diversity for solid-phase sequencing. In some embodiments, each of the overlapping primers also has at least one random nucleotide adjacent to the 5' start of the domain-specific sequence. In other embodiments, each of the overlapping primers has at least one degenerate nucleotide within the domain-specific sequence. In other embodiments, each of the overlapping primers has at least one random nucleotide adjacent to the 5' start of the domain-specific sequence, and also has at least one degenerate nucleotide within the domain-specific sequence.

The disclosed methods can be used with any sequencing methodology, but preferably incorporates high-throughput sequencing, such as solid surface-based sequencing. To facilitate these sequencing methods, the sequence of each primer in the amplification methods can include an adapter or partial adapter sequence so that the generated amplicon can be integrated into the sequencing technology. In specific embodiments, the partial adapter sequence in a forward primer is 5'-ACACTCTTTCCCTACACGACGCTCTTC-CGATCT (SEQ ID NO: 21). In other embodiments, the partial adapter sequence in a reverse primer is 5'-GACTG-GAGTTCAGACGTGTGCTCTTCCGATCT (SEQ ID NO: 22).

In some embodiments, the disclosed methods use several sets of forward, overlapping primers, in combination with several sets of reverse, overlapping primers. In some of these embodiments, the primers in a first forward primer set each have a domain-specific sequence that is substantially complementary to the C2-domain of the bacterial 16S DNA sequence ("C2-complementary" primers); the primers in a second forward primer set each have a domain-specific sequence that is substantially complementary to the C3-domain of the bacterial 16S DNA sequence ("C3-complementary" primers); the primers in a first reverse primer set each have a domain-specific sequence that is substantially complementary to the C4-domain of the bacterial 16S DNA sequence ("C4-complementary" primers); and the primers in a second reverse primer set each have a domain-specific sequence that is substantially complementary to the C5-domain of the bacterial 16S DNA sequence ("C5-complementary" primers). Using this combination of primers, frame-shifted amplicons are generated that include amplicons covering the V4 region, amplicons covering the V3 and V4 regions, amplicons covering the V4 and V5 regions, and amplicons covering the V3, V4 and V5 regions of the 16S DNA sequence.

Because the V4 amplicon would be the shortest amplicon generated by the above method, and therefore the most easily amplified sequence, care must be taken to avoid generating a disproportionate number of V4 amplicons, relative to the V3-V4, V4-V5, and V3-V4-V5 amplicons. The disclosed methods include a reaction scheme that involves three separate amplifications, performed effectively as two steps, that generates the desired amplicons while mimimizing this "V4 bias".

The two-step amplification method for generating V4, V3-V4, V4-V5, and V3-V4-V5 amplicons proceeds as follows. In the first step, DNA is amplified from a portion of a sample using the first set of forward, overlapping (C2-complementary) primers and the first set of reverse, overlapping (C4-complementary) primers to generate amplicons comprising the V3 and V4 regions. Additionally in the first step, DNA is amplified from a different portion of the same sample, using the second set of forward, overlapping (C3-complementary) primers and said second set of reverse, overlapping (C5-complementary) primers to generate amplicons comprising the V4 and V5 regions. The two amplifications in this first step can be performed at different times, or in parallel. In a specific embodiment, DNA amplification in each reaction proceeds via eight to twelve cycles of PCR, preferably ten cycles of PCR.

In the second step, the reaction mixtures generating V3-V4 and V4-V5 amplicons are pooled, and a third amplification reaction is performed. In this third reaction, DNA in the pooled mixture is amplified to generate a library of frame-shifted amplicons which include amplicons covering the V3 and V4 regions, amplicons covering the V4 and V5 regions, amplicons covering the V4 region, and amplicons covering the V3, V4, and V5 regions. This method generates each amplicon of interest, while avoiding V4 bias. In a specific embodiment, DNA amplification in this third reaction proceeds via five to seven cycles of PCR, preferably six cycles of PCR.

In some embodiments, each of the primers has an at least partial adapter sequence, and adapter primers and universal primers are added to the pooled reaction mixture of the second step, prior to performing the DNA amplification.

Following the final amplification step, the amplicons can then be isolated and sequenced by standard methods. For example, the amplicons may be sequenced by dye sequencing, pyrosequencing, or solid surface-based sequencing.

In a specific embodiment of this two-step amplification method, each primer in each forward and reverse primer set has an at least partial adapter sequence. In a further embodiment of this method, adapter primers and universal primers are added to the pooled reaction mixture prior to performing the third DNA amplification. The resulting amplicons, once isolated, are adapted for solid surface-based sequencing.

The present disclosure is further illustrated by the following non-limiting examples.

EXAMPLES

PCR Primer Selection

The inventors reviewed hundreds of documented 16S DNA primers to select primers as a basis for modification to achieve improved methods and primers for metagenomic analysis. Twenty-two primers were selected that could be suitable for modification and further analysis.

Primer Modification to Increase Diversity and Coverage of Microbial Species.

The inventors wished to be able to increase the number and diversity of species that could be identified by the primers, beyond the diversity of species that could be identified using prior art primers. In prior art identification of 16S DNA sequences for primer design, where there was any overlap between potential conserved sequences for design of primers, the prior art has taught to review and merge overlapping sequences to identify a single, "optimized" primer sequence that would encompass the most-conserved sequence between overlapping sequences (see, for example, Wang et al., *PLOS ONE* 4:e7401 (2009)). The prior art did not suggest the use of multiple sets of overlapping primers or creation of multiple frame-shifted amplicons for 16S analysis. However, the inventors hypothesized that simultaneous use of frame-shifted or overlapping primers in a composition for amplification might increase taxonomically-diverse sequence amplification. The inventors considered that overlapping primers could increase the chances that at least one primer will anneal to a target sequence in a mixture of diverse microbial species. The inventors further contemplated that increasing the numbers of different amplicons could increase library complexity, which could improve sequencing results if the resulting amplicons were sequenced using high-throughput sequencing technologies.

Figure 2:
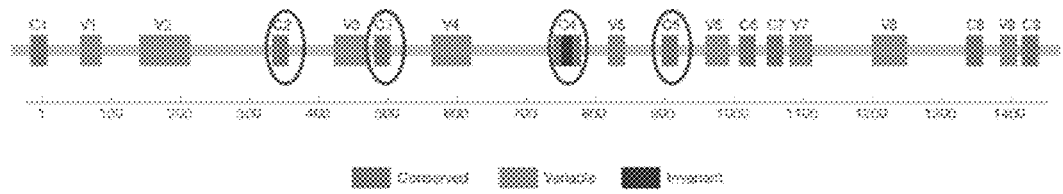
FIG. 2. Primers annealing to C2, C3, C4 and C5 regions were hand-picked and tested to achieve comprehensive coverage of microbial genomes present in a sample.

Therefore, the inventors designed and tested overlapping primers to anneal to the *E. coli* 16S DNA sequence at starting positions including (for V3-forward) positions 341, 343, 347, and 349 within conserved region C2; (for V4-forward) positions 515, 517, and 519 within conserved region C3; (for V4-reverse) positions 802, 803, 805, and 806 within conserved region C4; and (for V5-reverse) positions 926, 934 and 939 within conserved region C5 (FIG. 2). The inventors found that a "set" of two or more frame-shifted primers for amplification in one direction, paired with either a single primer for amplification in the opposite direction, or with a second set of frame-shifted primers for amplification in the opposite direction, can effectively identify a diversity of species in a sample.

To further increase diversity and coverage of microbial species, the inventors also modified the primers to introduce one or more degenerate nucleotides within the annealing sequence. The degenerate nucleotides were inserted at positions of known variability between species. Degenerate nucleotide positions were identified as follows: R (indicating A or G was inserted at that position), Y (C or T), S (G or C), W (A or T), K (G or T), M (A or C), B (C, G, or T), D (A, G, or T), H (A, C, or G), V (A, C, or G), or N or n (A, T, C, or G). Primers were further modified by introducing one to two random nucleotides (identified as "n", indicating any of A, T, C, or G was inserted) into each primer sequence, at the 5' start of the domain-specific sequence.

The 11 forward modified primers and 11 reverse modified primers were paired in many combinations individually and together with other pairs, and used to amplify DNA by PCR. *E. coli* and *P. furiosus* reference genomic DNA samples were used as templates to test the quality and compatibility of the modified primers. The PCR products were checked by electrophoresis. The PCR products from multiplex PCR were then cloned and sequenced by Sanger sequencing. Primers that resulted in nonspecific or weak amplification were modified or discarded.

After multiple rounds of testing, fifteen high quality gene-specific primers were selected that were capable of amplifying the V3, V4, and V5 hypervariable regions of the 16S ribosomal DNA sequence across many microbiotic taxa. These 15 gene-specific frame-shifted primers, with partial degeneracy and the presence of random nucleotides at the 5' end of the domain-specific sequence, can generate 124 variations of primer sequence. The primers were found to comprehensively cover many taxa of eubacteria and archaea. The variations in amplicon sequence resulting from the primer variations was found to increase library complexity and eliminate "spike in" as required by many high-throughput sequencing technologies for low complexity amplicon libraries.

The domain-specific portion of each of the fifteen gene-specific primers, including random nucleotides adjacent to the 5' start of the domain-specific sequence, and also including degenerate nucleotides within the domain-specific sequence, is provided as follows. In these sequences, "U" in the primer name indicates the primer is substantially complementary to all bacterial (universal) sequences, "E" in the primer name indicates the primer is substantially complementary to eubacterial sequences, "A" in the primer name indicates the primer is substantially complementary to archaebacterial sequences, "BE" in the primer name indicates the primer is substantially complementary to *Bifidobacterium* sequences; "F" in the primer name indicates a forward primer, and "R" in the primer name indicates a reverse primer; and "-n" indicates the presence of a random nucleotide:

U341F (SEQ ID NO: 23):
    nCCTACGGGRSGCAGCA

E343F (SEQ ID NO: 24):
    nTACGGRAGGCAGCAG

E347F (SEQ ID NO: 25):
    nGGAGGCAGCAGTRRGGAAT

E347F-n (SEQ ID NO: 26):
    nnGGAGGCAGCAGTRRGGAAT

A349F (SEQ ID NO: 27):
    nGYGCASCAGKCGMGAA

E802R (SEQ ID NO: 28):
    nTACNVGGGTATCTAATCC

E803R (SEQ ID NO: 29):
    nCTACCRGGGTATCTAATCC

U805R (SEQ ID NO: 30):
    nGACTACHVGGGTATCTAATCC

U805R-n (SEQ ID NO: 31):
    nnGACTACHVGGGTATCTAATCC

E806R (SEQ ID NO: 32):
    nGGACTACHVGGGTWTCTAAT

A806R (SEQ ID NO: 33):
    nGGACTACVSGGGTATCTAAT

U515F (SEQ ID NO: 34):
    nGTGYCAGCMGCCGCGGTAA

U515F-n (SEQ ID NO: 35):
    nnGTGYCAGCMGCCGCGGTAA

E517F (SEQ ID NO: 36):
    nGCCAGCAGCCGCGGTAA

A519F (SEQ ID NO: 37):
    nCAGCMGCCGCGGTAA

E939R (SEQ ID NO: 38):
    nCTTGTGCGGGCCCCCGTCAATTC

E939R-n (SEQ ID NO: 39):
    nnCTTGTGCGGGCCCCCGTCAATTC

A934R (SEQ ID NO: 40):
    nTCCCCCGCCAATTCCTTTAA

BE926R (SEQ ID NO: 41):
    nCCGTCAATTYMTTTRAGTtt

Primer Modification to Prepare for Amplification and Solid Support-based/DNA Colony Sequencing.

The primers were adapted for library construction by introducing into each primer sequence a partial adapter sequence for solid support-based/DNA colony amplification and sequencing.

To design primers for amplification and subsequent solid-support based/Illumina sequencing, the forward gene-specific primers were additionally modified to include an Illumina P5 partial adapter sequence, ACACTCTTTCCCTACACGACGCTCTTCCGATCT (SEQ ID NO: 21), at the 5' end, and the reverse primers were additionally modified to include an Illumina P7 partial adapter sequence, GACTGGAGTTCAGACGTGTGCTCTTCCGATCT (SEQ ID NO: 22), at the 5' end. Addition of the partial adapter sequence to the gene-specific primers allows the primers to be used with adapter primers, which would overlap with the partial adapter sequence of the gene-specific primers, and also with universal primers, to create amplicons suitable for Illumina sequencing. The scheme for amplicon generation is depicted in FIG. 3.

Generation of Amplicons by PCR

Amplicons were generated by PCR. PCR was designed by the inventors to involve short PCR cycles, to reduce sequencing bias. Two separate PCR reactions were performed in parallel: one to generate amplicons including the V3 and V4 regions, and one to generate amplicons including the V4 and V5 regions. Samples containing mixed microbial species were amplified in these two 25 µl multiplex PCR reactions, one reaction with the V3-forward and V4-reverse primer mix and one reaction with the V4-forward and V5-reverse primer pool. Each 25 µl PCR reaction contained 12.5 µl Invitrogen Platinum Multiplex master mix plus 2.5 µl GC enhancer (master mix and GC enhancer from Applied Biosystems, Carlsbad, Calif., USA), 2.5 µl of a mixture of the candidate 16S primers, and 50 ng of metagenomic DNA. Reactions were held at 95° C. for 2 min to denature the DNA, then proceeded through 10 cycles of 95° C. for 45 s, 57° C. for 90 s, and 72° C. for 50 s; a final extension of 72° C. for 10 minutes was added to ensure complete amplification.

To generate amplicons including V3 and V4 regions PCR was performed using a set of forward primers including U341F-p5, E343F-p5, E347F-p5, E347F-p5-n, and A349F-p5, and a set of reverse primers including E802R-p7, E803R-p7, U805R-p7, U805R-p7-n, E806R-p7, and A806R-p7. The primer sets had degenerate nucleotides within the domain-specific sequence (denoted according to standard degenerate code), as well as random nucleotides (denoted by "n") at the 5' end immediately preceding the domain-specific sequence. The primers for generation of V3-V4 region amplicons had the following sequences:

U341F-p5 (SEQ ID NO: 2):
ACACTCTTTCCCTACACGACGCTCTTCCGATCTnCCTACGGGRSGCAGCA

E343F-p5 (SEQ ID NO: 3):
ACACTCTTTCCCTACACGACGCTCTTCCGATCTnTACGGRAGGCAGCAG

E347F-p5 (SEQ ID NO: 4):
ACACTCTTTCCCTACACGACGCTCTTCCGATCTnGGAGGCAGCAGTRRGGAAT

E347F-p5-n (SEQ ID NO: 16):
ACACTCTTTCCCTACACGACGCTCTTCCGATCTnnGGAGGCAGCAGTRRGGAAT

A349F-p5 (SEQ ID NO: 5):
ACACTCTTTCCCTACACGACGCTCTTCCGATCTnGYGCASCAGKCGMGAA

E802R-p7 (SEQ ID NO: 9):
GACTGGAGTTCAGACGTGTGCTCTTCCGATCTnTACNVGGGTATCTAATCC

E803R-p7 (SEQ ID NO: 10):
GACTGGAGTTCAGACGTGTGCTCTTCCGATCTnCTACCRGGGTATCTAATCC

U805R-p7 (SEQ ID NO: 12):
GACTGGAGTTCAGACGTGTGCTCTTCCGATCTnGACTACHVGGGTATCTAATCC

U805R-p7-n (SEQ ID NO: 18):
GACTGGAGTTCAGACGTGTGCTCTTCCGATCTnnGACTACHVGGGTATCTAATCC

-continued

```
E806R-p7 (SEQ ID NO: 11):
GACTGGAGTTCAGACGTGTGCTCTTCCGATCTnGGACTACHVGGGTWTCT
AAT

A806R-p7 (SEQ ID NO: 13):
GACTGGAGTTCAGACGTGTGCTCTTCCGATCTnGGACTACVSGGGTATCT
AAT
```

To generate amplicons including the V4 and V5 regions, PCR was performed using a set of forward primers including U515F-p5, U515F-p5-n, E517F-p5, and A519F-p5, and a set of reverse primers including E939R-p7, E939R-p7-n, A934R-p7, and BE926R-p7. These primers also had degenerate nucleotides within the domain-specific sequence (denoted according to standard degenerate code as shown in Table 1), as well as random nucleotides (denoted by "n") immediately preceding the 5' end of the domain-specific sequence. The primers for generation of V4-V5 region amplicons had the following sequences:

```
U515F-p5 (SEQ ID NO: 6):
ACACTCTTTCCCTACACGACGCTCTTCCGATCTnGTGYCAGCMGCCGCGG
TAA

U515F-p5-n (SEQ ID NO: 17):
ACACTCTTTCCCTACACGACGCTCTTCCGATCTnnGTGYCAGCMGCCGCG
GTAA

E517F-p5 (SEQ ID NO: 7):
ACACTCTTTCCCTACACGACGCTCTTCCGATCTnGCCAGCAGCCGCGGTA
A

A519F-p5 (SEQ ID NO: 8):
ACACTCTTTCCCTACACGACGCTCTTCCGATCTnCAGCMGCCGCGGTAA

E939R-p7 (SEQ ID NO: 14):
GACTGGAGTTCAGACGTGTGCTCTTCCGATCTnCTTGTGCGGGCCCCGT
CAATTC

E939R-p7-n (SEQ ID NO: 19):
GACTGGAGTTCAGACGTGTGCTCTTCCGATCTnnCTTGTGCGGGCCCCG
TCAATTC

A934R-p7 (SEQ ID NO: 15):
GACTGGAGTTCAGACGTGTGCTCTTCCGATCTnTCCCCCGCCAATTCCTT
TAA

BE926R-p7 (SEQ ID NO: 20):
GACTGGAGTTCAGACGTGTGCTCTTCCGATCTnCCGTCAATTYMTTTRAG
Ttt
```

Library Preparation and Sequencing

After 10 rounds of PCR, the separate PCR reactions for V3-V4 and V4-V5 amplicons were combined and a third PCR was performed on the combined product to produce Illumina sequencing libraries. The following reagents were added to the PCR products: 12.5 μl Invitrogen Platinum Multiplex master mix with 2.5 μl GC enhancer (Applied Biosystems, Carlsbad, Calif., USA), 6 μl Illumina adapter primer mix, and 4 Illumina universal primer cocktail (Illumina Inc., San Diego, Calif., USA). Reactions were held at 95° C. for 2 min to denature the DNA, then 6 cycles of 95° C. for 45 sec, 57° C. for 90 sec, and 72° C. for 50 sec; a final extension of 72° C. for 10 minutes was added to ensure complete amplification. Amplicons from this final PCR included regions V3 to V4, V4 to V5, a short amplicon with V4 alone, and a long amplicon with the V3, V4, and V5 regions.

Specific universal primers in the universal primer cocktail had the sequences:

```
Universal primer-1.0 (SEQ ID NO: 42):
    AAT GAT ACG GCG ACC ACC GA

Universal primer-2.0 (SEQ ID NO: 43):
    CAA GCA GAA GAC GGC ATA CGA
```

The adapter primer mix had forward primers PD701-712 with 12 distinct barcodes, and reverse primers PD 501-508 with 8 distinct barcodes. Specific adapter primers included the following sequences, with the "barcode" indexing portion underlined, and "*" indicating the presence of a phosphorothioate bond between the 3' end C and T nucleotides:

```
PD501 (SEQ ID NO: 44):
AAT GAT ACG GCG ACC ACC GAG ATC TAC ACTATAGCCTAC
ACT CTT TCC CTA CAC GAC GCT CTT CCG ATC *T

PD502 (SEQ ID NO: 45):
AAT GAT ACG GCG ACC ACC GAG ATC TAC ACATAGAGGCAC
ACT CTT TCC CTA CAC GAC GCT CTT CCG ATC* T

PD503 (SEQ ID NO: 46):
AAT GAT ACG GCG ACC ACC GAG ATC TAC ACCCTATCCTAC
ACT CTT TCC CTA CAC GAC GCT CTT CCG ATC *T

PD504 (SEQ ID NO: 47):
AAT GAT ACG GCG ACC ACC GAG ATC TAC ACGGCTCTGAAC
ACT CTT TCC CTA CAC GAC GCT CTT CCG ATC *T

PD505 (SEQ ID NO: 48):
AAT GAT ACG GCG ACC ACC GAG ATC TAC ACAGGCGAAGAC
ACT CTT TCC CTA CAC GAC GCT CTT CCG ATC* T

PD506 (SEQ ID NO: 49):
AAT GAT ACG GCG ACC ACC GAG ATC TAC ACTAATCTTAAC
ACT CTT TCC CTA CAC GAC GCT CTT CCG ATC* T

PD507 (SEQ ID NO: 50):
AAT GAT ACG GCG ACC ACC GAG ATC TAC ACCAGGACGTAC
ACT CTT TCC CTA CAC GAC GCT CTT CCG ATC* T

PD508 (SEQ ID NO: 51):
AAT GAT ACG GCG ACC ACC GAG ATC TAC ACGTACTGACAC
ACT CTT TCC CTA CAC GAC GCT CTT CCG ATC* T

PD701 (SEQ ID NO: 52):
CAA GCA GAA GAC GGC ATA CGA GAT CGAGTAAT
GTG ACT GGA GTT CAG ACG TGT GCT CTT CCG ATC* T

PD702 (SEQ ID NO: 53):
CAA GCA GAA GAC GGC ATA CGA GAT TCTCCGGA
GTG ACT GGA GTT CAG ACG TGT GCT CTT CCG ATC *T

PD703 (SEQ ID NO: 54):
CAA GCA GAA GAC GGC ATA CGA GAT AATGAGCG
GTG ACT GGA GTT CAG ACG TGT GCT CTT CCG ATC* T
```

-continued

PD704 (SEQ ID NO: 55):
CAA GCA GAA GAC GGC ATA CGA GAT GGAATCTC

GTG ACT GGA GTT CAG ACG TGT GCT CTT CCG ATC *T

PD705 (SEQ ID NO: 56):
CAA GCA GAA GAC GGC ATA CGA GAT TTCTGAAT

GTG ACT GGA GTT CAG ACG TGT GCT CTT CCG ATC *T

PD706 (SEQ ID NO: 57):
CAA GCA GAA GAC GGC ATA CGA GAT ACGAATTC

GTG ACT GGA GTT CAG ACG TGT GCT CTT CCG ATC *T

PD707 (SEQ ID NO: 58):
CAA GCA GAA GAC GGC ATA CGA GAT AGCTTCAG

GTG ACT GGA GTT CAG ACG TGT GCT CTT CCG ATC* T

PD708 (SEQ ID NO: 59):
CAA GCA GAA GAC GGC ATA CGA GAT GCGCATTA

GTG ACT GGA GTT CAG ACG TGT GCT CTT CCG ATC* T

PD709 (SEQ ID NO: 60):
CAA GCA GAA GAC GGC ATA CGA GAT CATAGCCG

GTG ACT GGA GTT CAG ACG TGT GCT CTT CCG ATC* T

PD710 (SEQ ID NO: 61):
CAA GCA GAA GAC GGC ATA CGA GAT TTCGCGGA

GTG ACT GGA GTT CAG ACG TGT GCT CTT CCG ATC* T

PD711 (SEQ ID NO: 62):
CAA GCA GAA GAC GGC ATA CGA GAT GCGCGAGA

GTG ACT GGA GTT CAG ACG TGT GCT CTT CCG ATC* T

PD712 (SEQ ID NO: 63):
CAA GCA GAA GAC GGC ATA CGA GAT CTATCGCT

GTG ACT GGA GTT CAG ACG TGT GCT CTT CCG ATC* T

The amplicons were purified using Agencourt AMPure XP SPRI (Solid Phase Reversible Immobilization) magnetic beads (Beckman Coulter Co., Beverly, Mass., USA), according to the manufacturer's protocol. DNA libraries were validated using an Agilent 2100 Bioanalyzer (Agilent Technologies, Palo Alto, Calif., USA), and quantified by Qubit 2.0 Fluorometer (Invitrogen, Carlsbad, Calif., USA) and real time PCR (Applied Biosystems, Carlsbad, Calif., USA). DNA libraries were multiplexed based on index sequence and loaded on an Illumina MiSeq instrument according to manufacturer's instructions (Illumina Inc., San Diego, Calif., USA), except that no PhiX control DNA was added to the library mix. Sequencing was performed using a 2×150 paired-end (PE) configuration; image analysis and base calling were conducted by the MiSeq Control Software (MCS) on the MiSeq instrument. Initial taxonomy analysis was carried out on Illumina BaseSpace cloud computing platform (Illumina Inc., San Diego, Calif., USA).

As a control, the inventors also amplified the same metagenomic DNA using an established set of 16S primers. In brief, PCR amplification of the sample was performed using a single pair of primers, 515F/806R, to amplify the V4 region, along with three primers to generate Illumina sequencing libraries, according to the method and primers described in Caporaso et al., *Proc. Nat. Acad. Sci. USA* 108:4516-4522 (2011). Following amplification, V4 amplicons were purified, validated, quantified, and sequenced as above, with the exception that sequencing was performed with the addition of PhiX spike-in control DNA.

The inventors compared data generated using the established primers with data generated with the primers provided herein. The established primers generate only V4 amplicons ("V4-old"), while the disclosed primers and methods generate amplicons of V4, V3-V4, V4-V5, and a small amount of V3-V4-V5.

The inventors analyzed V4-old vs. V4-new, V4-old vs V3-V4, as well as V4-old vs. V4-V5. In addition, V3 alone was also included in the analysis. The inventors found that the detection capability using even just V3 is similar to the detection capability of V3-V4, V4 alone, or V4-V5. This shows that the method utilizing newly designed primers to generate the amplicons leads to increased detection ability across the 16S region.

In high throughput DNA colony sequencing with low library complexity (that is, many copies of identical or near-identical sequences), library complexity and ability to distinguish between distinct colonies of DNA clones must be artificially increased by adding control "spike-in" DNA of a different sequence than the sequence(s) of interest. This improves the detection capability of the sequencing platform, but wastes sequencing space and results in less total collection of data. The inventors thought that the use of primer pools of overlapping primers, random nucleotides, and degeneracy within the domain-specific sequence of the primers would lead to amplicons of sufficient diversity that control DNA would not be needed.

The inventors compared the quality of sequencing reads in high-throughput (Illumina) sequencing reactions using amplicons generated using primers of the invention and sequenced without presence of PhiX control DNA, with the quality of sequencing reads in Illumina sequencing reactions using amplicons generated using the method disclosed in Caporaso et al., and sequenced with addition of PhiX control DNA. The inventors found that the quality of sequencing data was comparable between amplicons generated with new primers and methods and amplicons generated with prior art primers and methods and sequenced with spike-in PhiX control DNA (FIGS. 4A-4D). This indicated that the new primers and methods provide high-quality sequencing data without the need to waste sequencing reads by adding control DNA.

Figure 8:
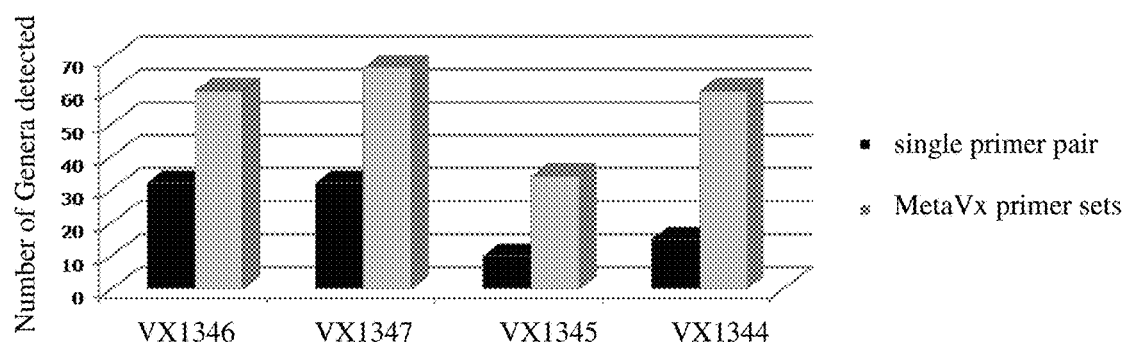
FIG. 8. Comparison of number of genera identified in samples VX1344, VX1345, VX1346, VX1347, by sequencing of amplicons generated using established method with single primer pair (black boxes) and sequencing of amplicons generated using new method and primer sets (grey boxes). For each sample, use of the new method and primer sets resulted in identification of two-fold (VX1346, VX1347), three-fold (VX1345), or even four-fold (VX1344) number of genera compared to established method and primers.

The inventors amplified and sequenced 16S DNA from samples of unknown composition utilizing the new primers and methods and also utilizing the "old" primers and method of Caporaso et al. The results are shown in FIGS. 5A-5B (Samples VX1344 and VX1345), 6A-6B (Samples VX1348 and VX1349), and 7A-7B (Samples VX1346 and VX1347). For each sample, the number of taxa identified using the "old" method was less than the number of taxa identified with the new primers and methods disclosed herein. Table 2 provides a comparison of kingdoms, phyla, classes, orders, families, and genera identified using the old method and new ("MetaVx") method, for sample VX1345. The inventors repeated these experiments with samples VX1344, VX1346, VX1347, VX1348, and VX1349. As seen in FIG. 8, use of the new method and primer sets resulted in identification of two-fold (VX1346, VX1347), three-fold (VX1345), or even four-fold (VX1344) number of genera compared to established methods and primers.

TABLE 2

Comparison of sequencing reads from amplification of sample VX1345 using old method and disclosed ("MetaVx") method.

| Level | Group | MetaVx Reads | Percentage | OLD Method Reads | Percentage |
|---|---|---|---|---|---|
| Kingdom | Bacteria | 1180932 | 99.95 | 773509 | 100.00 |
| Kingdom | Unclassified | 508 | 0.04 | 14 | 0.00 |
| Kingdom | Archaea | 135 | 0.01 | 13 | 0.00 |
| Phylum | Proteobacteria | 778853 | 65.92 | 552797 | 71.46 |
| Phylum | Nitrospirae | 365934 | 30.97 | 208630 | 26.97 |
| Phylum | Unclassified | 18597 | 1.57 | 14 | 0.00 |
| Phylum | Chlamydiae | 9001 | 0.76 | 4417 | 0.57 |
| Phylum | Actinobacteria | 6482 | 0.55 | 1712 | 0.22 |
| Phylum | Firmicutes | 1132 | 0.10 | 132 | 0.02 |
| Phylum | Bacteroidetes | 687 | 0.06 | 23 | 0.00 |
| Phylum | Spirochaetes | 451 | 0.04 | 25 | 0.00 |
| Phylum | Cyanobacteria | 351 | 0.03 | 170 | 0.02 |
| Class | Alphaproteobacteria | 613731 | 51.94 | 442798 | 57.24 |
| Class | Nitrospira (class) | 365934 | 30.97 | 208630 | 26.97 |
| Class | Gammaproteobacteria | 147730 | 12.50 | 105229 | 13.60 |
| Class | Unclassified | 33881 | 2.87 | 14 | 0.00 |
| Class | Chlamydiae (class) | 9001 | 0.76 | 4417 | 0.57 |
| Class | Actinobacteria (class) | 6482 | 0.55 | 1712 | 0.22 |
| Class | Betaproteobacteria | 1597 | 0.14 | 118 | 0.02 |
| Class | Bacilli | 874 | 0.07 | 73 | 0.01 |
| Class | Epsilonproteobacteria | 721 | 0.06 | 0 | 0.00 |
| Class | Sphingobacteria | 681 | 0.06 | 18 | 0.00 |
| Class | Spirochaetes (class) | 451 | 0.04 | 25 | 0.00 |
| Class | Clostridia | 197 | 0.02 | 34 | 0.00 |
| Class | Oscillatoriophycideae | 119 | 0.01 | 54 | 0.01 |
| Class | Nostocophycideae | 63 | 0.01 | 4 | 0.00 |
| Order | Rhodospirillales | 604295 | 51.14 | 438751 | 56.72 |
| Order | Nitrospirales | 365934 | 30.97 | 208630 | 26.97 |
| Order | Acidithiobacillales | 89359 | 7.56 | 67277 | 8.70 |
| Order | Unclassified | 68036 | 5.76 | 14 | 0.00 |
| Order | Salinisphaerales | 10576 | 0.90 | 0 | 0.00 |
| Order | Chlamydiales | 9001 | 0.76 | 4417 | 0.57 |
| Order | Chromatiales | 7322 | 0.62 | 33868 | 4.38 |
| Order | Rickettsiales | 6333 | 0.54 | 2324 | 0.30 |
| Order | Actinomycetales | 5403 | 0.46 | 1680 | 0.22 |
| Order | Enterobacteriales | 4745 | 0.40 | 173 | 0.02 |
| Order | Vibrionales | 1872 | 0.16 | 6 | 0.00 |
| Order | Burkholderiales | 1504 | 0.13 | 32 | 0.00 |
| Order | Bifidobacteriales | 1064 | 0.09 | 13 | 0.00 |
| Order | Xanthomonadales | 990 | 0.08 | 16 | 0.00 |
| Order | Thiotrichales | 824 | 0.07 | 43 | 0.01 |
| Order | Campylobacterales | 719 | 0.06 | 0 | 0.00 |
| Order | Sphingobacteriales | 681 | 0.06 | 18 | 0.00 |
| Order | Exiguobacterales | 492 | 0.04 | 18 | 0.00 |
| Order | Spirochaetales | 451 | 0.04 | 25 | 0.00 |
| Order | Rhodobacterales | 436 | 0.04 | 7 | 0.00 |
| Order | Bacillales | 332 | 0.03 | 37 | 0.00 |
| Order | Pseudomonadales | 277 | 0.02 | 5 | 0.00 |
| Order | Clostridiales | 197 | 0.02 | 17 | 0.00 |
| Order | Legionellales | 183 | 0.02 | 0 | 0.00 |
| Order | Oceanospirillales | 118 | 0.01 | 71 | 0.01 |
| Order | Chroococcales | 108 | 0.01 | 50 | 0.01 |
| Order | Nostocales | 63 | 0.01 | 4 | 0.00 |
| Family | Acetobacteraceae | 604218 | 51.14 | 438656 | 56.71 |
| Family | Leptospirillaceae | 365452 | 30.93 | 208388 | 26.94 |
| Family | Acidithiobacillaceae | 89359 | 7.56 | 67277 | 8.70 |
| Family | Unclassified | 78455 | 6.64 | 14 | 0.00 |
| Family | Salinisphaeraceae | 10576 | 0.90 | 0 | 0.00 |
| Family | Ectothiorhodospiraceae | 6562 | 0.56 | 33417 | 4.32 |
| Family | Rickettsiaceae | 5479 | 0.46 | 1815 | 0.23 |
| Family | Enterobacteriaceae | 4745 | 0.40 | 173 | 0.02 |
| Family | Mycobacteriaceae | 2309 | 0.20 | 1410 | 0.18 |
| Family | Corynebacteriaceae | 1974 | 0.17 | 0 | 0.00 |
| Family | Vibrionaceae | 1872 | 0.16 | 6 | 0.00 |
| Family | Burkholderiaceae | 1103 | 0.09 | 1 | 0.00 |
| Family | Bifidobacteriaceae | 1064 | 0.09 | 13 | 0.00 |
| Family | Xanthomonadaceae | 990 | 0.08 | 16 | 0.00 |
| Family | Endoecteinascidiaceae | 800 | 0.07 | 43 | 0.01 |
| Family | Campylobacteraceae | 719 | 0.06 | 0 | 0.00 |
| Family | Flexibacteraceae | 667 | 0.06 | 1 | 0.00 |
| Family | Candidatus Odyssella | 617 | 0.05 | 405 | 0.05 |
| Family | Rhabdochlamydiaceae | 552 | 0.05 | 569 | 0.07 |
| Family | Exiguobacteraceae | 492 | 0.04 | 18 | 0.00 |
| Family | Spirochaetaceae | 451 | 0.04 | 25 | 0.00 |

TABLE 2-continued

Comparison of sequencing reads from amplification of sample VX1345 using old method and disclosed ("MetaVx") method.

| Level | Group | MetaVx Reads | Percentage | OLD Method Reads | Percentage |
|---|---|---|---|---|---|
| Family | Rhodobacteraceae | 435 | 0.04 | 7 | 0.00 |
| Family | Alcaligenaceae | 379 | 0.03 | 3 | 0.00 |
| Family | Micrococcaceae | 357 | 0.03 | 29 | 0.00 |
| Family | Waddliaceae | 308 | 0.03 | 4 | 0.00 |
| Family | Pseudomonadaceae | 274 | 0.02 | 1 | 0.00 |
| Family | Bacillaceae | 264 | 0.02 | 25 | 0.00 |
| Family | (*Caedibacter*) | 201 | 0.02 | 102 | 0.01 |
| Family | Clostridiaceae | 191 | 0.02 | 8 | 0.00 |
| Family | Legionellaceae | 183 | 0.02 | 0 | 0.00 |
| Family | Parachlamydiaceae | 76 | 0.01 | 32 | 0.00 |
| Genus | *Acidiphilium* | 499085 | 42.24 | 367025 | 47.45 |
| Genus | *Leptospirillum* | 365452 | 30.93 | 208388 | 26.94 |
| Genus | Unclassified | 129155 | 10.93 | 14 | 0.00 |
| Genus | *Acidithiobacillus* | 89359 | 7.56 | 67277 | 8.70 |
| Genus | *Acidisoma* | 45280 | 3.83 | 62092 | 8.03 |
| Genus | *Acidisphaera* | 14487 | 1.23 | 0 | 0.00 |
| Genus | *Salinisphaera* | 10576 | 0.90 | 0 | 0.00 |
| Genus | *Arhodomonas* | 5235 | 0.44 | 31221 | 4.04 |
| Genus | *Orientia* | 2341 | 0.20 | 521 | 0.07 |
| Genus | *Mycobacterium* | 2309 | 0.20 | 1410 | 0.18 |
| Genus | *Corynebacterium* | 1974 | 0.17 | 0 | 0.00 |
| Genus | *Vibrio* | 1870 | 0.16 | 6 | 0.00 |
| Genus | *Rickettsia* | 1566 | 0.13 | 237 | 0.03 |
| Genus | *Salmonella* | 1202 | 0.10 | 3 | 0.00 |
| Genus | *Bifidobacterium* | 1041 | 0.09 | 12 | 0.00 |
| Genus | *Xylella* | 984 | 0.08 | 0 | 0.00 |
| Genus | *Burkholderia* | 936 | 0.08 | 0 | 0.00 |
| Genus | *Candidatus Endoecteinascidia* | 800 | 0.07 | 43 | 0.01 |
| Genus | *Campylobacter* | 719 | 0.06 | 0 | 0.00 |
| Genus | *Cytophaga* | 660 | 0.06 | 0 | 0.00 |
| Genus | *Candidatus Odyssella* | 617 | 0.05 | 405 | 0.05 |
| Genus | *Candidatus Rhabdochlamydia* | 552 | 0.05 | 569 | 0.07 |
| Genus | *Escherichia* | 538 | 0.05 | 6 | 0.00 |
| Genus | *Exiguobacterium* | 492 | 0.04 | 18 | 0.00 |
| Genus | *Borrelia* | 451 | 0.04 | 0 | 0.00 |
| Genus | *Bordetella* | 360 | 0.03 | 0 | 0.00 |
| Genus | *Waddlia* | 308 | 0.03 | 4 | 0.00 |
| Genus | *Shigella* | 306 | 0.03 | 8 | 0.00 |
| Genus | *Pseudomonas* | 272 | 0.02 | 1 | 0.00 |
| Genus | *Rhodobacter* | 240 | 0.02 | 0 | 0.00 |
| Genus | *Arthrobacter* | 239 | 0.02 | 7 | 0.00 |
| Genus | *Serratia* | 236 | 0.02 | 3 | 0.00 |
| Genus | *Leclercia* | 212 | 0.02 | 0 | 0.00 |
| Genus | *Caedibacter* | 201 | 0.02 | 102 | 0.01 |
| Genus | *Clostridium* | 191 | 0.02 | 8 | 0.00 |
| Genus | *Legionella* | 180 | 0.02 | 0 | 0.00 |
| Genus | *Bacillus* | 163 | 0.01 | 17 | 0.00 |
| Genus | *Cupriavidus* | 155 | 0.01 | 0 | 0.00 |
| Genus | *Virgibacillus* | 63 | 0.01 | 0 | 0.00 |
| Genus | *Klebsiella* | 60 | 0.01 | 0 | 0.00 |

What is claimed is:

1. A composition comprising a mixture of a forward primer set and a reverse primer set for identifying a plurality of microorganisms in a sample, wherein each primer set comprises one or more oligonucleotide primers, and at least one set comprises multiple primers;
   each primer comprises a domain-specific sequence that is substantially complementary to a conserved domain of a bacterial or archaeal ribosomal 16S DNA sequence adjacent to the V3, V4, or V5 region of said 16S DNA sequence; and
   for each primer set comprising multiple primers, the primers within the set are overlapping primers which are substantially complementary to the same conserved domain, and each primer within the set differs from at least another primer within the set by a frame shift of one to three nucleotides at the 5' end of the domain-specific sequence, such that said forward primer set and said reverse primer set generate frame-shifted amplicons in a polymerase-chain reaction (PCR), and wherein each primer in said composition further comprises an at least partial adapter sequence for facilitating sequencing of said sequence.

2. The composition of claim 1, wherein each primer in said primer set comprising multiple primers further comprises at least one random nucleotide adjacent to the 5' start of the domain-specific sequence.

3. The composition of claim 1, wherein the frame-shifted amplicons generated include amplicons comprising (i) the V3 and V4 regions; (ii) the V4 and V5 regions; (iii) the V4 region, and/or (iv) the V3, V4, and V5 regions.

4. The composition of claim 1, wherein the domain-specific sequence of each primer of the forward primer set is substantially complementary to the C2-domain of said 16S DNA sequence, and wherein the domain-specific sequence of each primer of the reverse primer set is substantially complementary to the C4-domain of said 16S DNA sequence.

5. The composition of claim 1, wherein the domain-specific sequence of each primer of the forward primer set is substantially complementary to the C3-domain of said 16S DNA sequence, and wherein the domain-specific sequence of each primer of the reverse primer set is substantially complementary to the CS-domain of said 16S DNA sequence.

6. The composition of claim 1, wherein both the forward primer set and the reverse primer set comprise multiple overlapping primers.

7. The composition of claim 6, comprising:
   a first set of forward, overlapping primers, wherein the domain-specific sequence of each primer of the first forward primer set is substantially complementary to the C2-domain of said 16S DNA sequence;
   a second set of forward, overlapping primers, wherein the domain-specific sequence of each primer of the second forward primer set is substantially complementary to the C3-domain of said 16S DNA sequence;
   a first set of reverse, overlapping primers, wherein the domain-specific sequence of each primer of the first reverse primer set is substantially complementary to the C4-domain of said 16S DNA sequence; and
   a second set of reverse, overlapping primers, wherein the domain-specific sequence of each primer of the second reverse primer set is substantially complementary to the CS-domain of said 16S DNA sequence, such that the frame-shifted amplicons generated include amplicons comprising the V4 region, amplicons comprising the V3 and V4 regions, amplicons comprising the V4 and V5 regions, and amplicons comprising the V3, V4, and V5 regions.

8. The composition of claim 1, further comprising at least one pair of forward and reverse adapter oligonucleotide primers that are substantially complementary to the at least partial adapter sequence of said oligonucleotide primers.

9. The composition of claim 8, further comprising at least one pair of forward and reverse universal oligonucleotide primers that are substantially complementary to the adapter oligonucleotide primers.

10. The composition of claim 1, wherein said oligonucleotide primers are selected from the group consisting of SEQ ID NO: 2 through SEQ ID NO: 20.

11. The composition of claim 10, wherein said composition comprises two or more oligonucleotide forward primers selected from SEQ ID NOS: 2, 3, 4, 5, 6, 7, 8, 16, and 17, and two or more oligonucleotide reverse primers selected from SEQ ID NOS: 9, 10, 11, 12, 13, 14, 15, 18, 19, and 20.

12. The composition of claim 11, wherein said composition comprises two or more oligonucleotide forward primers selected from SEQ ID NOS: 2, 3, 4, 5, and 16, and two or more oligonucleotide reverse primers selected from SEQ ID NOS: 9, 10, 11, 12, 13, and 18, for amplification of V3 to V4 regions.

13. The composition of claim 12, wherein said composition comprises two or more oligonucleotide forward primers selected from SEQ ID NOS: 6, 7, 8, and 17, and two or more oligonucleotide reverse primers selected from SEQ ID NOS: 14, 15, 19, and 20, for amplification of V4 to V5 regions.

14. A method to identify a plurality of microorganisms in a sample, the method comprising:
 a. amplifying DNA from said sample with a forward primer set and a reverse primer set, each primer set comprising one or more oligonucleotide primers, and at least one set comprises multiple primers; each primer comprising a domain-specific sequence that is substantially complementary to a conserved domain of a bacterial or archaeal ribosomal 16S DNA sequence adjacent to the V3, V4, or V5 region of said 16S DNA sequence; and wherein for each primer set comprising multiple primers, the primers within the set are overlapping primers which are substantially complementary to the same conserved domain, and each primer within the set differs from at least another primer within the set by a frame shift of one to three nucleotides at the 5' end of the domain-specific sequence, such that said forward primer set and said reverse primer set generate frame-shifted amplicons;
 b. isolating the generated frame-shifted amplicons from the amplified DNA;
 c. sequencing the isolated amplicons; and
 d. identifying microorganisms present in said sample based on identification of species-specific 16S DNA sequences in the amplicons generated from said sample.

15. The method of claim 14, wherein each primer in said primer set comprising multiple primers further comprises at least one random nucleotide adjacent to the 5' start of the domain-specific sequence.

16. The method of claim 14 or 15, wherein each primer in said primer set comprising multiple primers further comprises at least one degenerate nucleotide within the domain-specific sequence.

17. The method of claim 14, wherein the oligonucleotide primers in step (a) comprise:
 a first set of forward, overlapping primers, wherein the domain-specific sequence of each primer of the first forward primer set is substantially complementary to the C2-domain of said 16S DNA sequence;
 a second set of forward, overlapping primers, wherein the domain-specific sequence of each primer of the second forward primer set is substantially complementary to the C3-domain of said 16S DNA sequence;
 a first set of reverse, overlapping primers, wherein the domain-specific sequence of each primer of the first reverse primer set is substantially complementary to the C4-domain of said 16S DNA sequence; and
 a second set of reverse, overlapping primers, wherein the domain-specific sequence of each primer of the second reverse primer set is substantially complementary to the C5-domain of said 16S DNA sequence,
such that the frame-shifted amplicons generated in step (a) include amplicons comprising the V4 region, amplicons comprising the V3 and V4 regions, amplicons comprising the V4 and V5 regions, and amplicons comprising the V3, V4 and V5 regions.

18. The method of claim 17, wherein said amplification step (a) comprises:
 i. amplifying DNA from a portion of said sample using said first set of forward, overlapping primers and the first set of reverse, overlapping primers to generate amplicons comprising the V3 and V4 regions;
 ii. amplifying DNA from a different portion of said sample using said second set of forward, overlapping primers and said second set of reverse, overlapping primers to generate amplicons comprising the V4 and V5 regions;
 iii. pooling the reaction mixtures from steps (i) and (ii); and
 iv. amplifying DNA in the pooled mixture to generate a library of frame-shifted amplicons which include amplicons comprising the V3 and V4 regions, amplicons comprising the V4 and V5 regions, amplicons comprising the V4 region, and amplicons comprising the V3, V4, and V5 regions.

19. The method of claim 18, wherein each of the oligonucleotide primers further comprise an at least partial adapter sequence.

20. The method of claim 19, wherein adapter primers and universal primers are added to the pooled reaction mixture of step (iii) prior to performing DNA amplification in step (iv).

21. The method of claim 18, wherein said DNA amplification in step (i) and (ii) each comprises eight to twelve cycles of PCR, and the DNA amplification in step iv comprises five to seven cycles of PCR.

22. The method of claim 19, wherein said amplified DNA is sequenced using dye sequencing or pyrosequencing.

23. The compostion of claim 1, wherein each primer in said primer set comprising multiple primers further comprises at least one degenerate nucleotide within the domain-specific sequence.

* * * * *

SEQUENCE LISTING

<160> NUMBER OF SEQ ID NOS: 63

<210> SEQ ID NO 1
<211> LENGTH: 1542
<212> TYPE: RNA
<213> ORGANISM: Escherichia coli

<400> SEQUENCE: 1

```
aaauugaaga guuugaucau ggcucagauu gaacgcuggc ggcaggccua acacaugcaa    60
gucgaacggu aacaggaagc agcuugcugc uucgcugacg aguggcggac gggugaguaa   120 ugucgggaa gcugccugau ggaggggau aacuacugga aacgguagcu aauaccgcau    180
```

| | |
|---|---|
| aaugucgcaa gaccaaagag ggggaccuuc gggccucuug ccaucggaug ugcccagaug | 240 |
| ggauuagcuu guuggugggg uaacggcuca ccaaggcgac gaucccuagc uggucugaga | 300 |
| ggaugaccag ccacacugga acugagacac gguccagacu ccuacgggag gcagcagugg | 360 |
| ggaauauugc acaauggggcg caagccugau gcagccaugc cgcguguaug aagaaggccu | 420 |
| ucggguugua aaguacuuuc agcggggagg aagggaguaa aguuaauacc uuugcucauu | 480 |
| gacguuaccc gcagaagaag caccggcuaa cuccgugcca gcagccgcgg uaauacggag | 540 |
| ggugcaagcg uuaaucggaa uuacugggcg uaaagcgcac gcaggcgguu uguuaaguca | 600 |
| gaugugaaau ccccgggcuc aaccgggaa cugcaucuga uacuggcaag cuugagucuc | 660 |
| guagaggggg guagaauucc aggugagcg gugaaaugcg uagagaucug gaggaauacc | 720 |
| gguggcgaag gcggccccu ggacgaagac ugacgcucag gugcgaaagc gggggagca | 780 |
| aacaggauua gauacccugg uaguccacgc cguaaacgau gucgacuugg agguugugcc | 840 |
| cuugaggcgu ggcuuccgga gcuaacgcgu uaagucgacc gccuggggag uacggccgca | 900 |
| agguuaaaac ucaaaugaau ugacgggggc ccgcacaagc gguggagcau gugguuuaau | 960 |
| ucgaugcaac gcgaagaacc uuaccugguc uugacaucca cggaaguuuu cagagaugag | 1020 |
| aaugugccuu cgggaaccgu gagacaggug cugcauggcu gucgucagcu cguguuguga | 1080 |
| aauguugggu uaagucccgc aacgagcgca acccuuaucc uuuguugcca gcggccggc | 1140 |
| cgggaacuca aaggagacug ccagugauaa acuggaggaa ggugggggaug acgucaaguc | 1200 |
| aucauggccc uuacgaccag ggcuacacac gugcuacaau ggcgcauaca aagagaagcg | 1260 |
| accucgcgag agcaagcgga ccucauaaag ugcgucguag uccggauugg agucugcaac | 1320 |
| ucgacuccau gaagucggaa ucgcuaguaa ucguggauca gaaugccacg gugaauacgu | 1380 |
| ucccgggccu uguacacacc gcccgucaca ccaugggagu ggguugcaaa agaaguaggu | 1440 |
| agcuuaaccu ucggggaggc gcuuaccacu uugugauuca ugacuggggu gaagucguaa | 1500 |
| caagguaacc guaggggaac cugcgguugg aucaccuccu ua | 1542 |

<210> SEQ ID NO 2
<211> LENGTH: 50
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(34)
<223> OTHER INFORMATION: n is a, c, g, or t

<400> SEQUENCE: 2
acactctttc cctacacgac gctcttccga tctncctacg ggrsgcagca                50

<210> SEQ ID NO 3
<211> LENGTH: 49
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(34)
<223> OTHER INFORMATION: n is a, c, g, or t

<400> SEQUENCE: 3
acactctttc cctacacgac gctcttccga tctntacggr aggcagcag                49

<210> SEQ ID NO 4
<211> LENGTH: 53
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(34)
<223> OTHER INFORMATION: n is a, c, g, or t

<400> SEQUENCE: 4
acactctttc cctacacgac gctcttccga tctnggaggc agcagtrrgg aat            53

<210> SEQ ID NO 5
<211> LENGTH: 50
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(34)
<223> OTHER INFORMATION: n is a, c, g, or t

<400> SEQUENCE: 5
acactctttc cctacacgac gctcttccga tctngygcas cagkcgmgaa               50

<210> SEQ ID NO 6
<211> LENGTH: 53
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(34)
<223> OTHER INFORMATION: n is a, c, g, or t

<400> SEQUENCE: 6
acactctttc cctacacgac gctcttccga tctngtgyca gcmgccgcgg taa            53

<210> SEQ ID NO 7
<211> LENGTH: 51
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(34)
<223> OTHER INFORMATION: n is a, c, g, or t

<400> SEQUENCE: 7
acactctttc cctacacgac gctcttccga tctngccagc agccgcggta a              51

<210> SEQ ID NO 8
<211> LENGTH: 49
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(34)
<223> OTHER INFORMATION: n is a, c, g, or t

<400> SEQUENCE: 8
acactctttc cctacacgac gctcttccga tctncagcmg ccgcggtaa                49

<210> SEQ ID NO 9
<211> LENGTH: 52
<212> TYPE: DNA
<213> ORGANISM: Artificial Sequence
<220> FEATURE:
<223> OTHER INFORMATION: synthetic seqnence
<220> FEATURE:
<221> NAME/KEY: misc_feature
<222> LOCATION: (33)..(33)
<223> OTHER INFORMATION: n is a, c, g, or t

<400> SEQUENCE: 9
gactggagtt cagacgtgtg ctcttccgat ctnctaccrg ggtatctaat cc    52

<210> SEQ ID NO 10
<211> LENGTH: 52
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(33)
<223> OTHER INFORMATION: n is a, c, g, or t

<400> SEQUENCE: 10
gactggagtt cagacgtgtg ctcttccgat ctnctaccrg ggtatctaat cc    52

<210> SEQ ID NO 11
<211> LENGTH: 53
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(33)
<223> OTHER INFORMATION: n is a, c, g, or t

<400> SEQUENCE: 11
gactggagtt cagacgtgtg ctcttccgat ctnggactac hvgggtwtct aat    53

<210> SEQ ID NO 12
<211> LENGTH: 54
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(33)
<223> OTHER INFORMATION: n is a, c, g, or t

<400> SEQUENCE: 12
gactggagtt cagacgtgtg ctcttccgat ctngactach vgggtatcta atcc    54

<210> SEQ ID NO 13
<211> LENGTH: 53
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(33)
<223> OTHER INFORMATION: n is a, c, g, or t

<400> SEQUENCE: 13
gactggagtt cagacgtgtg ctcttccgat ctnggactac vsgggtatct aat    53

<210> SEQ ID NO 14
<211> LENGTH: 56
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(33)
<223> OTHER INFORMATION: n is a, c, g, or t

<400> SEQUENCE: 14
gactggagtt cagacgtgtg ctcttccgat ctncttgtgc gggcccccgt caattc    56

<210> SEQ ID NO 15
<211> LENGTH: 53
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(33)
<223> OTHER INFORMATION: n is a, c, g, or t

<400> SEQUENCE: 15
gactggagtt cagacgtgtg ctcttccgat ctntcccccg ccaattcctt taa    53

<210> SEQ ID NO 16
<211> LENGTH: 54
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(35)
<223> OTHER INFORMATION: n is a, c, g, or t

<400> SEQUENCE: 16
acactctttc cctacacgac gctcttccga tctnnggagg cagcagtrrg gaat    54

<210> SEQ ID NO 17
<211> LENGTH: 54
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(35)
<223> OTHER INFORMATION: n is a, c, g, or t

<400> SEQUENCE: 17
acactctttc cctacacgac gctcttccga tctnngtgyc agcmgccgcg gtaa    54

<210> SEQ ID NO 18
<211> LENGTH: 55
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(34)
<223> OTHER INFORMATION: n is a, c, g, or t

<400> SEQUENCE: 18
gactggagtt cagacgtgtg ctcttccgat ctnngactac hvgggtatct aatcc          55

<210> SEQ ID NO 19
<211> LENGTH: 57
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(34)
<223> OTHER INFORMATION: n is a, c, g, or t

<400> SEQUENCE: 19
gactggagtt cagacgtgtg ctcttccgat ctnncttgtg cgggccccg tcaattc          57

<210> SEQ ID NO 20
<211> LENGTH: 53
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (33)..(33)
<223> OTHER INFORMATION: n is a, c, g, or t

<400> SEQUENCE: 20
gactggagtt cagacgtgtg ctcttccgat ctnccgtcaa ttymtttrag ttt             53

<210> SEQ ID NO 21
<211> LENGTH: 33
<212> TYPE: DNA
<213> ORGANISM: Artificial Sequence
<220> FEATURE:
<223> OTHER INFORMATION: synthetic sequence

<400> SEQUENCE: 21
acactctttc cctacacgac gctcttccga tct                                   33

<210> SEQ ID NO 22
<211> LENGTH: 32
<212> TYPE: DNA
<213> ORGANISM: Artificial Sequence
<220> FEATURE:
<223> OTHER INFORMATION: synthetic sequence

<400> SEQUENCE: 22
gactggagtt cagacgtgtg ctcttccgat ct                                    32

<210> SEQ ID NO 23
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 23
ncctacgggr sgcagca                                                     17

<210> SEQ ID NO 24
<211> LENGTH: 16
<212> TYPE: DNA

```
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 24
ntacggragg cagcag                                                    16

<210> SEQ ID NO 25
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 25
nggaggcagc agtrrggaat                                                20

<210> SEQ ID NO 26
<211> LENGTH: 21
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: n is a, c, g, or t

<400> SEQUENCE: 26
nnggaggcag cagtrrggaa t                                              21

<210> SEQ ID NO 27
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 27
ngygcascag kcgmgaa                                                   17

<210> SEQ ID NO 28
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 28
ntacnvgggt atctaatcc                                                 19
```

<210> SEQ ID NO 29
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 29
nctaccrggg tatctaatcc                                               20

<210> SEQ ID NO 30
<211> LENGTH: 22
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 30
ngactachvg ggtatctaat cc                                            22

<210> SEQ ID NO 31
<211> LENGTH: 23
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: n is a, c, g, or t

<400> SEQUENCE: 31
nngactachv gggtatctaa tcc                                           23

<210> SEQ ID NO 32
<211> LENGTH: 21
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 32
nggactachv gggtwtctaa t                                             21

<210> SEQ ID NO 33
<211> LENGTH: 21
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 33
nggactacvs gggtatctaa t                                              21

<210> SEQ ID NO 34
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 34
ngtgycagcm gccgcggtaa                                                20

<210> SEQ ID NO 35
<211> LENGTH: 21
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: n is a, c, g, or t

<400> SEQUENCE: 35
nngtgycagc mgccgcggta a                                              21

<210> SEQ ID NO 36
<211> LENGTH: 18
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 36
ngccagcagc cgcggtaa                                                  18

<210> SEQ ID NO 37
<211> LENGTH: 16
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 37
ncagcmgccg cggtaa                                                    16

<210> SEQ ID NO 38
<211> LENGTH: 24
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 38

-continued

```
ncttgtgcgg gcccccgtca attc                                          24

<210> SEQ ID NO 39
<211> LENGTH: 25
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: n is a, c, g, or t

<400> SEQUENCE: 39
nncttgtgcg ggcccccgtc aattc                                         25

<210> SEQ ID NO 40
<211> LENGTH: 21
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 40
ntcccccgcc aattccttta a                                             21

<210> SEQ ID NO 41
<211> LENGTH: 21
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is a, c, g, or t

<400> SEQUENCE: 41
nccgtcaatt ymtttragtt t                                             21

<210> SEQ ID NO 42
<211> LENGTH: 20
<212> TYPE: DNA
<213> ORGANISM: Artificial Sequence
<220> FEATURE:
<223> OTHER INFORMATION: synthetic sequence

<400> SEQUENCE: 42
aatgatacgg cgaccaccga                                               20

<210> SEQ ID NO 43
<211> LENGTH: 21
<212> TYPE: DNA
<213> ORGANISM: Artificial Sequence
<220> FEATURE:
<223> OTHER INFORMATION: synthetic sequence

<400> SEQUENCE: 43
caagcagaag acggcatacg a                                             21

<210> SEQ ID NO 44
<211> LENGTH: 70
<212> TYPE: DNA
```

<213> ORGANISM: Artificial Sequence
<220> FEATURE:
<223> OTHER INFORMATION: synthetic sequence

<400> SEQUENCE: 44
aatgatacgg cgaccaccga gatctacact atagcctaca ctctttccct acacgacgct    60
cttccgatct                                                          70

<210> SEQ ID NO 45
<211> LENGTH: 70
<212> TYPE: DNA
<213> ORGANISM: Artificial Sequence
<220> FEATURE:
<223> OTHER INFORMATION: synthetic sequence

<400> SEQUENCE: 45
aatgatacgg cgaccaccga gatctacaca tagaggcaca ctctttccct acacgacgct    60
cttccgatct                                                          70

<210> SEQ ID NO 46
<211> LENGTH: 70
<212> TYPE: DNA
<213> ORGANISM: Artificial Sequence
<220> FEATURE:
<223> OTHER INFORMATION: synthetic sequence

<400> SEQUENCE: 46
aatgatacgg cgaccaccga gatctacacc ctatcctaca ctctttccct acacgacgct    60
cttccgatct                                                          70

<210> SEQ ID NO 47
<211> LENGTH: 70
<212> TYPE: DNA
<213> ORGANISM: Artificial Sequence
<220> FEATURE:
<223> OTHER INFORMATION: synthetic sequence

<400> SEQUENCE: 47
aatgatacgg cgaccaccga gatctacacg gctctgaaca ctctttccct acacgacgct    60
cttccgatct                                                          70

<210> SEQ ID NO 48
<211> LENGTH: 70
<212> TYPE: DNA
<213> ORGANISM: Artificial Sequence
<220> FEATURE:
<223> OTHER INFORMATION: synthetic sequence

<400> SEQUENCE: 48
aatgatacgg cgaccaccga gatctacaca ggcgaagaca ctctttccct acacgacgct    60
cttccgatct                                                          70

<210> SEQ ID NO 49
<211> LENGTH: 70
<212> TYPE: DNA
<213> ORGANISM: Artificial Sequence
<220> FEATURE:
<223> OTHER INFORMATION: synthetic sequence

<400> SEQUENCE: 49
aatgatacgg cgaccaccga gatctacact aatcttaaca ctctttccct acacgacgct    60
cttccgatct                                                          70

<210> SEQ ID NO 50
<211> LENGTH: 70
<212> TYPE: DNA
<213> ORGANISM: Artificial Sequence
<220> FEATURE:
<223> OTHER INFORMATION: synthetic sequence

<400> SEQUENCE: 50
aatgatacgg cgaccaccga gatctacacc aggacgtaca ctctttccct acacgacgct    60
cttccgatct                                                          70

<210> SEQ ID NO 51
<211> LENGTH: 70
<212> TYPE: DNA
<213> ORGANISM: Artificial Sequence
<220> FEATURE:
<223> OTHER INFORMATION: synthetic sequence

<400> SEQUENCE: 51
aatgatacgg cgaccaccga gatctacacg tactgacaca ctctttccct acacgacgct    60
cttccgatct                                                          70

<210> SEQ ID NO 52
<211> LENGTH: 66
<212> TYPE: DNA
<213> ORGANISM: Artificial Sequence
<220> FEATURE:
<223> OTHER INFORMATION: synthetic sequence

<400> SEQUENCE: 52
caagcagaag acggcatacg agatcgagta atgtgactgg agttcagacg tgtgctcttc    60
cgatct                                                              66

<210> SEQ ID NO 53
<211> LENGTH: 66
<212> TYPE: DNA
<213> ORGANISM: Artificial Sequence
<220> FEATURE:
<223> OTHER INFORMATION: synthetic sequence

<400> SEQUENCE: 53
caagcagaag acggcatacg agattctccg gagtgactgg agttcagacg tgtgctcttc    60
cgatct                                                              66

<210> SEQ ID NO 54
<211> LENGTH: 66
<212> TYPE: DNA
<213> ORGANISM: Artificial Sequence
<220> FEATURE:
<223> OTHER INFORMATION: synthetic sequence

<400> SEQUENCE: 54
caagcagaag acggcatacg agataatgag cggtgactgg agttcagacg tgtgctcttc    60
cgatct                                                              66

<210> SEQ ID NO 55
<211> LENGTH: 66
<212> TYPE: DNA
<213> ORGANISM: Artificial Sequence
<220> FEATURE:
<223> OTHER INFORMATION: synthetic sequence

<400> SEQUENCE: 55
caagcagaag acggcatacg agatggaatc tcgtgactgg agttcagacg tgtgctcttc        60
cgatct                                                                   66

<210> SEQ ID NO 56
<211> LENGTH: 66
<212> TYPE: DNA
<213> ORGANISM: Artificial Sequence
<220> FEATURE:
<223> OTHER INFORMATION: synthetic sequence

<400> SEQUENCE: 56
caagcagaag acggcatacg agatttctga atgtgactgg agttcagacg tgtgctcttc        60
cgatct                                                                   66

<210> SEQ ID NO 57
<211> LENGTH: 66
<212> TYPE: DNA
<213> ORGANISM: Artificial Sequence
<220> FEATURE:
<223> OTHER INFORMATION: synthetic sequence

<400> SEQUENCE: 57
caagcagaag acggcatacg agatacgaat tcgtgactgg agttcagacg tgtgctcttc        60
cgatct                                                                   66

<210> SEQ ID NO 58
<211> LENGTH: 66
<212> TYPE: DNA
<213> ORGANISM: Artificial Sequence
<220> FEATURE:
<223> OTHER INFORMATION: synthetic sequence

<400> SEQUENCE: 58
caagcagaag acggcatacg agatagcttc aggtgactgg agttcagacg tgtgctcttc        60
cgatct                                                                   66

<210> SEQ ID NO 59
<211> LENGTH: 66
<212> TYPE: DNA
<213> ORGANISM: Artificial Sequence
<220> FEATURE:
<223> OTHER INFORMATION: synthetic sequence

<400> SEQUENCE: 59
caagcagaag acggcatacg agatgcgcat tagtgactgg agttcagacg tgtgctcttc        60
cgatct                                                                   66

<210> SEQ ID NO 60
<211> LENGTH: 66
<212> TYPE: DNA
<213> ORGANISM: Artificial Sequence
<220> FEATURE:
<223> OTHER INFORMATION: synthetic sequence

<400> SEQUENCE: 60
caagcagaag acggcatacg agatcatagc cggtgactgg agttcagacg tgtgctcttc        60
cgatct                                                                   66

<210> SEQ ID NO 61
<211> LENGTH: 66

```
<212> TYPE: DNA
<213> ORGANISM: Artificial Sequence
<220> FEATURE:
<223> OTHER INFORMATION: synthetic sequence

<400> SEQUENCE: 61
caagcagaag acggcatacg agatttcgcg gagtgactgg agttcagacg tgtgctcttc    60
cgatct                                                              66

<210> SEQ ID NO 62
<211> LENGTH: 66
<212> TYPE: DNA
<213> ORGANISM: Artificial Sequence
<220> FEATURE:
<223> OTHER INFORMATION: synthetic sequence

<400> SEQUENCE: 62
caagcagaag acggcatacg agatgcgcga gagtgactgg agttcagacg tgtgctcttc    60
cgatct                                                              66

<210> SEQ ID NO 63
<211> LENGTH: 66
<212> TYPE: DNA
<213> ORGANISM: Artificial Sequence
<220> FEATURE:
<223> OTHER INFORMATION: synthetic sequence

<400> SEQUENCE: 63
caagcagaag acggcatacg agatctatcg ctgtgactgg agttcagacg tgtgctcttc    60
cgatct                                                              66
```